US012600771B2

(12) United States Patent
Zheng et al.

(10) Patent No.: US 12,600,771 B2
(45) Date of Patent: Apr. 14, 2026

(54) ANTIBODY FOR BINDING TO INTERLEUKIN 4 RECEPTOR

(71) Applicant: SuZhou Connect Biopharmaceuticals, Ltd, Taicang (CN)

(72) Inventors: Wei Zheng, San Diego, CA (US); Wubin Pan, Richmond (CA); Xin Yang, Taicang (CN); Yang Chen, Taicang (CN); Limin Zhang, Taicang (CN); Jie Jiang, Taicang (CN)

(73) Assignee: CONNECT BIOPHARMA HONGKONG LIMITED, Kowloon (HK)

( * ) Notice: Subject to any disclaimer, the term of this patent is extended or adjusted under 35 U.S.C. 154(b) by 89 days.

(21) Appl. No.: 18/510,553

(22) Filed: Nov. 15, 2023

(65) Prior Publication Data

US 2024/0190954 A1 Jun. 13, 2024

Related U.S. Application Data

(60) Division of application No. 16/994,464, filed on Aug. 14, 2020, now Pat. No. 11,866,491, which is a division of application No. 16/809,411, filed on Mar. 4, 2020, now Pat. No. 10,774,141, which is a continuation of application No. 16/307,930, filed as application No. PCT/CN2017/087592 on Jun. 8, 2017, now abandoned.

(30) Foreign Application Priority Data

Jun. 8, 2016 (CN) .......................... 201610399254.4

(51) Int. Cl.
| | |
|---|---|
| A61K 39/395 | (2006.01) |
| A61P 29/00 | (2006.01) |
| A61P 37/08 | (2006.01) |
| C07K 16/24 | (2006.01) |
| C07K 16/28 | (2006.01) |
| C12N 5/12 | (2006.01) |
| C12N 15/62 | (2006.01) |
| C12N 15/85 | (2006.01) |
| A61K 38/00 | (2006.01) |
| A61K 45/06 | (2006.01) |

(52) U.S. Cl.
CPC .......... *C07K 16/247* (2013.01); *A61K 39/395* (2013.01); *A61P 29/00* (2018.01); *A61P 37/08* (2018.01); *C07K 16/28* (2013.01); *C12N 5/12* (2013.01); *C12N 15/62* (2013.01); *C12N 15/85* (2013.01); *A61K 38/00* (2013.01); *A61K 45/06* (2013.01); *C12N 2015/8518* (2013.01)

(58) Field of Classification Search
CPC ............ A61K 39/395; A61K 2039/505; C07K 14/7155; C07K 2317/76; C07K 16/2866; C07K 2317/565
See application file for complete search history.

(56) References Cited

U.S. PATENT DOCUMENTS

| | | | |
|---|---|---|---|
| 7,638,606 B2 | 12/2009 | Carter | |
| 8,679,487 B2 | 3/2014 | Armitage et al. | |
| 9,290,574 B2 | 3/2016 | Kostic et al. | |
| 9,334,331 B2 * | 5/2016 | Igawa ..................... | A61P 43/00 |
| 10,421,807 B2 * | 9/2019 | Gonzales ................ | A61P 43/00 |
| 10,485,844 B2 | 11/2019 | Radin et al. | |
| 10,730,948 B2 | 8/2020 | Kostic et al. | |
| 10,774,141 B2 | 9/2020 | Zheng et al. | |
| 11,866,491 B2 | 1/2024 | Zheng et al. | |
| 2016/0363591 A1 | 12/2016 | Streicher et al. | |
| 2018/0016343 A1 | 1/2018 | Ardeleanu et al. | |
| 2019/0040126 A1 | 2/2019 | Radin et al. | |
| 2019/0177408 A1 | 6/2019 | Zheng et al. | |
| 2019/0183973 A1 | 6/2019 | Hamilton et al. | |
| 2019/0345253 A1 | 11/2019 | Bansal | |
| 2019/0367622 A1 | 12/2019 | Graham et al. | |
| 2019/0367624 A1 | 12/2019 | Dix et al. | |
| 2020/0283518 A1 | 9/2020 | Liot et al. | |

FOREIGN PATENT DOCUMENTS

| | | |
|---|---|---|
| CN | 1886426 A | 12/2006 |
| CN | 101522716 A | 9/2009 |
| CN | 103998053 A | 8/2014 |
| CN | 107474134 A | 12/2017 |
| CN | 108339118 A | 7/2018 |
| CN | 109789196 A | 5/2019 |
| CN | 111526920 A | 8/2020 |
| CN | 111686247 A | 9/2020 |
| CN | 111939261 A | 11/2020 |
| CN | 112153982 A | 12/2020 |
| EP | 2292665 A1 | 3/2011 |

(Continued)

OTHER PUBLICATIONS

Poosarla et al. (2017), Biotechn. Bioeng. 114(6): 1331-1342.*

(Continued)

*Primary Examiner* — Gyan Chandra

(74) *Attorney, Agent, or Firm* — Mintz Levin Cohn Ferris Glovsky and Popeo PC

(57) ABSTRACT

Disclosed is an antibody capable of binding to the interleukin 4 (IL-4) receptor (IL-4). Also disclosed are a nucleic acid sequence encoding the antibody, a vector including the nucleic acid sequence, and a host cell transformed or transfected with the vector. Provided are a method for producing the antibody, a medical use of the antibody, and a kit including the antibody.

30 Claims, 5 Drawing Sheets

Specification includes a Sequence Listing.

(56)                References Cited

FOREIGN PATENT DOCUMENTS

| EP | 2990420 | B1 | 12/2016 |
|----|---------|----|---------|
| EP | 2892927 | B1 | 5/2018 |
| EP | 3354663 | A1 | 8/2018 |
| EP | 3470430 | A1 | 4/2019 |
| JP | 2017-527560 | A | 9/2017 |
| RU | 2663106 | C2 | 8/2018 |
| WO | WO-01/92340 | A2 | 12/2001 |
| WO | WO-2005/047325 | A2 | 5/2005 |
| WO | WO-2005/047331 | A2 | 5/2005 |
| WO | WO-2008/054606 | A2 | 5/2008 |
| WO | WO-2009/121847 | A2 | 10/2009 |
| WO | WO-2010/070346 | A2 | 6/2010 |
| WO | WO-2012071372 | A2 | 5/2012 |
| WO | WO-2013/087660 | A1 | 6/2013 |
| WO | WO-2015/130975 | A1 | 9/2015 |
| WO | WO-2018/045130 | A1 | 3/2018 |
| WO | WO-2018/057776 | A1 | 3/2018 |
| WO | WO-2019/089473 | A1 | 5/2019 |
| WO | WO-2020/096381 | A1 | 5/2020 |
| WO | WO-2020/180727 | A1 | 9/2020 |
| WO | WO-2020/182197 | A1 | 9/2020 |

OTHER PUBLICATIONS

Kaji et al, (Journal of Experimental Medicine; (2012); vol. 209, pp. 2079-2097.*

Khan et al. (2014), J. Immunol. 192: 5398-5405.*
Goel et al. (2004), J. Immunol. 173: 7358-7367.*
Lloyd et al. (2009, Protein Engineering, Eng. Design & Selection 22(3): 159-168).*
Edwards et al. (2003), JMB 334:103-118.*
Rudikoff et al., Proc. Natl. Acad. Sci. 79: 1979-1983, (1982).*
Al Qaraghuli et al., Nature Scientific Reports 10:13969, (2020).*
Rabia, et al. (2018), Biochemical Engineering Journal 137:365-374.*
Angal et al., A Single Amino Acid Substitution Abolishes the Heterogeneity of Chimeric Mouse/Human (IgG4) Antibody, Mol Immunol. 1993; 30:105-08.
Brorson et al. (J. Immunol. 163:6694-6701 (1999)).
Brummell et al. (Biochemistry 32:1180-1187 (1993)).
Burks et al. (PNAS 94:412-417 (1997)).
Casset et al (Biochemical and Biophysical Research Communications, 307:198-205, 2003).
Coleman (Research in Immunol. 145:33-36 (1994)).
International Search Report dated Aug. 25, 2017 for corresponding PCT Application No. PCT/CN2017/087592 (7 pages).
Kau et al., Current Opinion Allergy Clinical Immunology, 2014, vol. 14. No. 6, pp. 570-575.
Kobayashi et al. (Protein Engineering 12:879-844 (1999)).
Le Floch et al., (Allergy. 2020; vol. 75, pp. 188-1204).
Supplementary European Search Report for International Application No. EP17809758, Apr. 22, 2020, 22 pages.

* cited by examiner

ANTIBODY FOR BINDING TO INTERLEUKIN 4 RECEPTOR

CROSS-REFERENCE TO RELATED APPLICATIONS

The present application is a divisional of U.S. application Ser. No. 16/994,464, filed on Aug. 14, 2020 (now issued as U.S. Pat. No. 11,866,491 on Jan. 9, 2024), which is a divisional of U.S. application Ser. No. 16/809,411, filed Mar. 4, 2020 (now issued as U.S. Pat. No. 10,774,141 on Sep. 15, 2020), which is a continuation application of U.S. application Ser. No. 16/307,930, filed Dec. 6, 2018, which is the National Stage of International Application Number PCT/CN2017/087592, filed on Jun. 8, 2017, which claims priority of Chinese Patent Application Number 201610399254.4, filed on Jun. 8, 2016, the entire contents of each of which are incorporated herein by reference.

INCORPORATION BY REFERENCE

The instant application contains a Sequence Listing which has been filed electronically in XML format and is hereby incorporated by reference in its entirety. Said XML file copy, created on Nov. 15, 2023, is named CBP-001C1D2.xml and is 123,329 bytes in size.

TECHNICAL FIELD

The present invention relates to the field of biopharmaceutics. Particularly, the present invention relates to an antibody that is capable of binding to interleukin 4 (IL-4) receptor (IL-4R) and uses thereof.

BACKGROUND OF THE INVENTION

Interleukin-4 (IL-4) is a cytokine produced primarily by activated T cells, monocytes, basophils, mast cells, and eosinophils. IL-4 is involved in a variety of biological processes, and its biological effects known in the art include stimulating the proliferation of activated B cells and T cells and the differentiation of CD4+ T cells into type II helper T cells. What's more, studies have shown that IL-4 has multiple effects in mediating immune responses to diseases such as allergic diseases, autoimmune diseases, infectious diseases and tumors, and has therapeutic effects on tumors, autoimmune diseases and infectious diseases and the like. Meanwhile, IL-4 can also regulate immune response to vaccine. Therefore, IL-4 has always been one hot area for research attracting extensive attentions.

IL-13 is also a cytokine produced by activated T cells, which has different functions in different types of cells, such as monocytes, B cells, mast cells and keratinocytes. IL-13 can inhibit the release of inflammatory cytokines and chemokines from monocytes, induce the proliferation and differentiation of B cells, and promote the synthesis of IgE. IL-13 and IL-4 share many common properties in terms of biological functions, including inhibiting the release of inflammatory mediators from monocytes, inducing dendritic-like development of macrophages, promoting the expression of CD23 on the surface of monocytes and stimulating the synthesis of immunoglobulins by B cells. At the same time, IL-13 also has its own biological features, mainly including: promoting the differentiation of human monocytes and changes of antigens on cell surface; inducing the proliferation and differentiation of B cells, and promoting the secretion of antibodies from B cells; regulating the synthesis of IgE, thereby being associated with allergic reactions in the body; inhibiting the growth of tumor cells; inhibiting the replication of HIV; and the like.

The biological activity of IL-4 is mediated by a specific IL-4 receptor on cell surface (IL-4R, which is called "hIL-4R" in human). Human IL-4R is a heterodimer formed by two polypeptide chains, in which the alpha chain (hIL-4Rα, UniProtKB: P24394) has a high affinity for IL-4. And studies have shown that the cell surface receptor alpha chain of IL-13 (IL-13Rα chain) also forms another form of IL-4R complex with IL-4Rα chain. Since the IL-4Rα chain in the IL-4R complex plays a leading role in binding to IL-4 and other cytokines are involved, the IL-4Rα chain is currently being studied as a major target. What's more, human monoclonal antibodies against the IL-4Rα chain have been clinically proven to be effective in relieving and treating conditions such as asthma, eczema, atopic dermatitis and the like.

Human interleukin-4 receptor is known to produce a soluble form of protein (shIL-4Rα, SEQ ID NO: 94) that inhibits cell proliferation mediated by IL-4 and IL-5 up-regulation mediated by T cells. Two forms of the receptor are associated with allergic reaction, which manifests as diseases like allergic rhinitis, sinusitis, asthma, eczema and so on. Therefore, blocking antibodies that target the protein can help treat and relieve said diseases.

Asthma is a chronic airway inflammatory disease, in which many inflammatory cells, such as eosnophils, mast cells and lymphocytes are involved, and its specific pathogenesis is still unclear. Since cytokines such as IL-4 play an important role in the occurrence and development of bronchial asthma, the development of antibodies specific for IL-4 is one of the effective ways to treat asthma. Inhibition of IL-4/IL-4Rα can have an effective immunomodulatory effect on asthma.

Allergic rhinitis (AR) has a pathogenesis much in common with that of asthma, and it and asthma both belong to type I allergy. Meanwhile, studies have found that IL-4, IL-17 and IgE play an important role in the pathogenesis of allergic rhinitis. So far, drug therapy is the focus of AR treatment, in which intranasal corticosteroids and antihistamines are at the core position.

Atopic dermatitis (AD), also known as heterotopic dermatitis or hereditary allergic dermatitis, is a common dermatological disease that is mostly seen in children and adolescents, and is often complicated with certain hereditary allergic diseases such as allergic rhinitis, asthma and the like. The involvement of immunological factors such as IL-4 and IL-13 are one of the main pathogenesis.

Eosinophilic esophagitis (EoE) is a chronic immune inflammatory disease characterized by infiltration of eosinophils (EOS) in all layers of esophagus. The onset of EoE is associated with dysfunction of Th2 cells. At present, protocols with high specificity, such as novel biological agent anti-IL-5 (such as mepolizumab) have become hotspots in research. Although immune-modulating therapy has achieved results in animal models, explorations are still needed in human clinical trials. Medicaments such as PGD2 inhibitors, anti-TNF-α, and anti-IL-13 are under investigation at present.

Monoclonal antibody medicaments targeting the hIL-4R have now entered clinical trials, such as Dupilumab, which has shown good efficacy in phase II clinical trial of atopic dermatitis. In addition to Dupilumab, other monoclonal antibodies against hIL-4R have been claimed in patent applications by companies, for example U.S. Pat. Nos. 7,186,809 and 7,638,606.

SUMMARY OF THE INVENTION

The present invention provides an antibody specific for IL-4R through antibody screening and optimization, and the antibody can serve as a blocking agent for the binding of IL-4 to IL-4R, and can be used for treating inflammation or allergic diseases by binding to IL-4R.

With reference to the numbering of amino acid residues of the sequence as set forth in SEQ ID NO: 58, the antibody of the present invention has a serine at position 31 (31Ser) of the light chain variable region comprised therein, and with reference to the numbering of amino acid residues of the sequence as set forth in SEQ ID NO: 93, the antibody has an aspartic acid at position 103 (103Asp), and a tyrosine at position 104 (104Tyr) of the heavy chain variable region comprised therein. Wherein, the 31Ser is located in CDR1 of the light chain variable region of the present antibody correspondingly, and the 103Asp and 104Tyr are located in the CDR3 of the heavy chain variable region of the present antibody correspondingly.

Preferably, the light chain variable region of the present antibody comprises CDR1 as set forth in SEQ ID NO: 2, and the heavy variable region of the antibody comprises CDR3 as set forth in SEQ ID NO: 19.

Preferably, the light chain variable region of the present antibody comprises a combination of CDR1, CDR2, and CDR3 selected from the group consisting of:

(1) CDR1 as set forth in SEQ ID NO: 2, CDR2 as set forth in SEQ ID NO: 3 and CDR3 as set forth in SEQ ID NO: 5;

(2) CDR1 as set forth in SEQ ID NO: 2, CDR2 as set forth in SEQ ID NO: 4 and CDR3 as set forth in SEQ ID NO: 5;

(3) CDR1 as set forth in SEQ ID NO: 2, CDR2 as set forth in SEQ ID NO: 3 and CDR3 as set forth in SEQ ID NO: 6;

(4) CDR1 as set forth in SEQ ID NO: 2, CDR2 as set forth in SEQ ID NO: 3 and CDR3 as set forth in SEQ ID NO: 7;

(5) CDR1 as set forth in SEQ ID NO: 2, CDR2 as set forth in SEQ ID NO: 3 and CDR3 as set forth in SEQ ID NO: 8;

(6) CDR1 as set forth in SEQ ID NO: 2, CDR2 as set forth in SEQ ID NO: 4 and CDR3 as set forth in SEQ ID NO: 6;

(7) CDR1 as set forth in SEQ ID NO: 2, CDR2 as set forth in SEQ ID NO: 4 and CDR3 as set forth in SEQ ID NO: 7; and (8) CDR1 as set forth in SEQ ID NO: 2, CDR2 as set forth in SEQ ID NO: 4 and CDR3 as set forth in SEQ ID NO: 8; and the heavy chain variable region of the present antibody comprises a combination of CDR1, CDR2, and CDR3 selected from the group consisting of:

(1) CDR1 as set forth in SEQ ID NO: 14, CDR2 as set forth in SEQ ID NO: 17 and CDR3 as set forth in SEQ ID NO: 19;

(2) CDR1 as set forth in SEQ ID NO: 14, CDR2 as set forth in SEQ ID NO: 18 and CDR3 as set forth in SEQ ID NO: 19;

(3) CDR1 as set forth in SEQ ID NO: 15, CDR2 as set forth in SEQ ID NO: 17 and CDR3 as set forth in SEQ ID NO: 19;

(4) CDR1 as set forth in SEQ ID NO: 15, CDR2 as set forth in SEQ ID NO: 18 and CDR3 as set forth in SEQ ID NO: 19;

(5) CDR1 as set forth in SEQ ID NO: 16, CDR2 as set forth in SEQ ID NO: 18 and CDR3 as set forth in SEQ ID NO: 19; and (6) CDR1 as set forth in SEQ ID NO: 16, CDR2 as set forth in SEQ ID NO: 17 and CDR3 as set forth in SEQ ID NO: 19.

More preferably, the present invention antibody comprises a light chain variable region selected from the amino acid sequences shown in the following sequences: SEQ ID NO: 40, SEQ ID NO: 41, SEQ ID NO: 44, SEQ ID NO: 45, SEQ ID NO: 46, SEQ ID NO: 47, SEQ ID NO: 49, SEQ ID NO: 50, SEQ ID NO: 51, SEQ ID NO: 54, SEQ ID NO: 55 and SEQ ID NO: 57, and the antibody comprises a heavy chain variable region selected from the amino acid sequences shown in the following sequences: SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 91 and SEQ ID NO: 92.

Further preferably, the present antibody comprises a combination of a light chain variable region and a heavy chain variable region selected from the group consisting of:

(1) a light chain variable region as set forth in SEQ ID NO: 57 and a heavy chain variable region as set forth in SEQ ID NO: 62;

(2) a light chain variable region as set forth in SEQ ID NO: 57 and a heavy chain variable region as set forth in SEQ ID NO: 63;

(3) a light chain variable region as set forth in SEQ ID NO: 57 and a heavy chain variable region as set forth in SEQ ID NO: 59;

(4) a light chain variable region as set forth in SEQ ID NO: 57 and a heavy chain variable region as set forth in SEQ ID NO: 60;

(5) a light chain variable region as set forth in SEQ ID NO: 57 and a heavy chain variable region as set forth in SEQ ID NO: 61;

(6) a light chain variable region as set forth in SEQ ID NO: 57 and a heavy chain variable region as set forth in SEQ ID NO: 67;

(7) a light chain variable region as set forth in SEQ ID NO: 57 and a heavy chain variable region as set forth in SEQ ID NO: 65;

(8) a light chain variable region as set forth in SEQ ID NO: 57 and a heavy chain variable region as set forth in SEQ ID NO: 66;

(9) a light chain variable region as set forth in SEQ ID NO: 57 and a heavy chain variable region as set forth in SEQ ID NO: 64;

(10) a light chain variable region as set forth in SEQ ID NO: 57 and a heavy chain variable region as set forth in SEQ ID NO: 91;

(11) a light chain variable region as set forth in SEQ ID NO: 57 and a heavy chain variable region as set forth in SEQ ID NO: 74;

(12) a light chain variable region as set forth in SEQ ID NO: 57 and a heavy chain variable region as set forth in SEQ ID NO: 75;

(13) a light chain variable region as set forth in SEQ ID NO: 57 and a heavy chain variable region as set forth in SEQ ID NO: 76;

(14) a light chain variable region as set forth in SEQ ID NO: 57 and a heavy chain variable region as set forth in SEQ ID NO: 77;

(15) a light chain variable region as set forth in SEQ ID NO: 57 and a heavy chain variable region as set forth in SEQ ID NO: 78;

(16) a light chain variable region as set forth in SEQ ID NO: 57 and a heavy chain variable region as set forth in SEQ ID NO: 80;

(17) a light chain variable region as set forth in SEQ ID NO: 40 and a heavy chain variable region as set forth in SEQ ID NO: 92;

(18) a light chain variable region as set forth in SEQ ID NO: 41 and a heavy chain variable region as set forth in SEQ ID NO: 92;

(19) a light chain variable region as set forth in SEQ ID NO: 44 and a heavy chain variable region as set forth in SEQ ID NO: 92;

(20) a light chain variable region as set forth in SEQ ID NO: 44 and a heavy chain variable region as set forth in SEQ ID NO: 62;

(21) a light chain variable region as set forth in SEQ ID NO: 44 and a heavy chain variable region as set forth in SEQ ID NO: 91;

(22) a light chain variable region as set forth in SEQ ID NO: 49 and a heavy chain variable region as set forth in SEQ ID NO: 92;

(23) a light chain variable region as set forth in SEQ ID NO: 50 and a heavy chain variable region as set forth in SEQ ID NO: 92;

(24) a light chain variable region as set forth in SEQ ID NO: 45 and a heavy chain variable region as set forth in SEQ ID NO: 92;

(25) a light chain variable region as set forth in SEQ ID NO: 46 and a heavy chain variable region as set forth in SEQ ID NO: 92;

(26) a light chain variable region as set forth in SEQ ID NO: 47 and a heavy chain variable region as set forth in SEQ ID NO: 92;

(27) a light chain variable region as set forth in SEQ ID NO: 55 and a heavy chain variable region as set forth in SEQ ID NO: 92;

(28) a light chain variable region as set forth in SEQ ID NO: 55 and a heavy chain variable region as set forth in SEQ ID NO: 62;

(29) a light chain variable region as set forth in SEQ ID NO: 55 and a heavy chain variable region as set forth in SEQ ID NO: 91;

(30) a light chain variable region as set forth in SEQ ID NO: 54 and a heavy chain variable region as set forth in SEQ ID NO: 92;

(31) a light chain variable region as set forth in SEQ ID NO: 54 and a heavy chain variable region as set forth in SEQ ID NO: 62;

(32) a light chain variable region as set forth in SEQ ID NO: 54 and a heavy chain variable region as set forth in SEQ ID NO: 91; and

(33) a light chain variable region as set forth in SEQ ID NO: 51 and a heavy chain variable region as set forth in SEQ ID NO: 92.

In another aspect, the present invention provides an antibody that can bind to Interleukin 4 (IL-4) receptor (IL-4R). The antibody comprises a light chain variable region (VL), and the light chain variable region comprises a combination of CDR1, CDR2 and CDR3 selected from the group consisting of:

(1) CDR1 as set forth in SEQ ID NO: 1, CDR2 as set forth in SEQ ID NO: 3 and CDR3 as set forth in SEQ ID NO: 5;

(2) CDR1 as set forth in SEQ ID NO: 2, CDR2 as set forth in SEQ ID NO: 3 and CDR3 as set forth in SEQ ID NO: 5;

(3) CDR1 as set forth in SEQ ID NO: 2, CDR2 as set forth in SEQ ID NO: 4 and CDR3 as set forth in SEQ ID NO: 5;

(4) CDR1 as set forth in SEQ ID NO: 1, CDR2 as set forth in SEQ ID NO: 4 and CDR3 as set forth in SEQ ID NO: 5;

(5) CDR1 as set forth in SEQ ID NO: 2, CDR2 as set forth in SEQ ID NO: 3 and CDR3 as set forth in SEQ ID NO: 6;

(6) CDR1 as set forth in SEQ ID NO: 2, CDR2 as set forth in SEQ ID NO: 3 and CDR3 as set forth in SEQ ID NO: 7;

(7) CDR1 as set forth in SEQ ID NO: 2, CDR2 as set forth in SEQ ID NO: 3 and CDR3 as set forth in SEQ ID NO: 8;

(8) CDR1 as set forth in SEQ ID NO: 1, CDR2 as set forth in SEQ ID NO: 3 and CDR3 as set forth in SEQ ID NO: 6;

(9) CDR1 as set forth in SEQ ID NO: 2, CDR2 as set forth in SEQ ID NO: 4 and CDR3 as set forth in SEQ ID NO: 6;

(10) CDR1 as set forth in SEQ ID NO: 2, CDR2 as set forth in SEQ ID NO: 4 and CDR3 as set forth in SEQ ID NO: 8;

(11) CDR1 as set forth in SEQ ID NO: 1, CDR2 as set forth in SEQ ID NO: 4 and CDR3 as set forth in SEQ ID NO: 8 and

(12) CDR1 as set forth in SEQ ID NO: 1, CDR2 as set forth in SEQ ID NO: 3 and CDR3 as set forth in SEQ ID NO: 8;

and/or the antibody comprises a heavy chain variable region (VH), and the heavy chain variable region comprises a combination of CDR1, CDR2 and CDR3 selected from the group consisting of:

(1) CDR1 as set forth in SEQ ID NO: 14, CDR2 as set forth in SEQ ID NO: 17 and CDR3 as set forth in SEQ ID NO: 19;

(2) CDR1 as set forth in SEQ ID NO: 14, CDR2 as set forth in SEQ ID NO: 18 and CDR3 as set forth in SEQ ID NO: 19;

(3) CDR1 as set forth in SEQ ID NO: 14, CDR2 as set forth in SEQ ID NO: 17 and CDR3 as set forth in SEQ ID NO: 20;

(4) CDR1 as set forth in SEQ ID NO: 14, CDR2 as set forth in SEQ ID NO: 18 and CDR3 as set forth in SEQ ID NO: 20;

(5) CDR1 as set forth in SEQ ID NO: 15, CDR2 as set forth in SEQ ID NO: 17 and CDR3 as set forth in SEQ ID NO: 19;

(6) CDR1 as set forth in SEQ ID NO: 16, CDR2 as set forth in SEQ ID NO: 17 and CDR3 as set forth in SEQ ID NO: 19; and (7) CDR1 as set forth in SEQ ID NO: 14, CDR2 as set forth in SEQ ID NO: 18 and CDR3 as set forth in SEQ ID NO: 19.

Further, with regard to framework regions of the antibody of the present invention as described above, the light chain variable region of the present antibody preferably comprises a combination of FR1, FR2, FR3 and FR4 selected from the group consisting of:

(1) FR1 as set forth in SEQ ID NO: 9, FR2 as set forth in SEQ ID NO: 10, FR3 as set forth in SEQ ID NO: 12 and FR4 as set forth in SEQ ID NO: 13; and (2) FR1 as set forth in SEQ ID NO: 9, FR2 as set forth in SEQ ID NO: 11, FR3 as set forth in SEQ ID NO: 12 and FR4 as set forth in SEQ ID NO: 13.

Preferably, the heavy chain variable region of the antibody comprises a combination of FR1, FR2, FR3 and FR4 selected from the group consisting of:

(1) FR1 as set forth in SEQ ID NO: 21, FR2 as set forth in SEQ ID NO: 32, FR3 as set forth in SEQ ID NO: 34 and FR4 as set forth in SEQ ID NO: 38;

(2) FR1 as set forth in SEQ ID NO: 22, FR2 as set forth in SEQ ID NO: 32, FR3 as set forth in SEQ ID NO: 34 and FR4 as set forth in SEQ ID NO: 38;

(3) FR1 as set forth in SEQ ID NO: 23, FR2 as set forth in SEQ ID NO: 32, FR3 as set forth in SEQ ID NO: 34 and FR4 as set forth in SEQ ID NO: 38;

(4) FR1 as set forth in SEQ ID NO: 24, FR2 as set forth in SEQ ID NO: 32, FR3 as set forth in SEQ ID NO: 34 and FR4 as set forth in SEQ ID NO: 38;

(5) FR1 as set forth in SEQ ID NO: 24, FR2 as set forth in SEQ ID NO: 32, FR3 as set forth in SEQ ID NO: 35 and FR4 as set forth in SEQ ID NO: 38;

(6) FR1 as set forth in SEQ ID NO: 25, FR2 as set forth in SEQ ID NO: 32, FR3 as set forth in SEQ ID NO: 34 and FR4 as set forth in SEQ ID NO: 38;

(7) FR1 as set forth in SEQ ID NO: 26, FR2 as set forth in SEQ ID NO: 32, FR3 as set forth in SEQ ID NO: 34 and FR4 as set forth in SEQ ID NO: 38;

(8) FR1 as set forth in SEQ ID NO: 27, FR2 as set forth in SEQ ID NO: 32, FR3 as set forth in SEQ ID NO: 34 and FR4 as set forth in SEQ ID NO: 38;

(9) FR1 as set forth in SEQ ID NO: 29, FR2 as set forth in SEQ ID NO: 32, FR3 as set forth in SEQ ID NO: 34 and FR4 as set forth in SEQ ID NO: 38;

(10) FR1 as set forth in SEQ ID NO: 30, FR2 as set forth in SEQ ID NO: 32, FR3 as set forth in SEQ ID NO: 34 and FR4 as set forth in SEQ ID NO: 38;

(11) FR1 as set forth in SEQ ID NO: 24, FR2 as set forth in SEQ ID NO: 33, FR3 as set forth in SEQ ID NO: 34 and FR4 as set forth in SEQ ID NO: 38;

(12) FR1 as set forth in SEQ ID NO: 24, FR2 as set forth in SEQ ID NO: 32, FR3 as set forth in SEQ ID NO: 36 and FR4 as set forth in SEQ ID NO: 38;

(13) FR1 as set forth in SEQ ID NO: 24, FR2 as set forth in SEQ ID NO: 32, FR3 as set forth in SEQ ID NO: 37 and FR4 as set forth in SEQ ID NO: 38;

(14) FR1 as set forth in SEQ ID NO: 31, FR2 as set forth in SEQ ID NO: 32, FR3 as set forth in SEQ ID NO: 34 and FR4 as set forth in SEQ ID NO: 38;

(15) FR1 as set forth in SEQ ID NO: 27, FR2 as set forth in SEQ ID NO: 32, FR3 as set forth in SEQ ID NO: 35 and FR4 as set forth in SEQ ID NO: 38;

(16) FR1 as set forth in SEQ ID NO: 26, FR2 as set forth in SEQ ID NO: 32, FR3 as set forth in SEQ ID NO: 35 and FR4 as set forth in SEQ ID NO: 38;

(17) FR1 as set forth in SEQ ID NO: 25, FR2 as set forth in SEQ ID NO: 32, FR3 as set forth in SEQ ID NO: 35 and FR4 as set forth in SEQ ID NO: 38;

(18) FR1 as set forth in SEQ ID NO: 28, FR2 as set forth in SEQ ID NO: 32, FR3 as set forth in SEQ ID NO: 35 and FR4 as set forth in SEQ ID NO: 38;

(19) FR1 as set forth in SEQ ID NO: 28, FR2 as set forth in SEQ ID NO: 32, FR3 as set forth in SEQ ID NO: 34 and FR4 as set forth in SEQ ID NO: 38;

(20) FR1 as set forth in SEQ ID NO: 23, FR2 as set forth in SEQ ID NO: 32, FR3 as set forth in SEQ ID NO: 35 and FR4 as set forth in SEQ ID NO: 38;

(21) FR1 as set forth in SEQ ID NO: 22, FR2 as set forth in SEQ ID NO: 32, FR3 as set forth in SEQ ID NO: 35 and FR4 as set forth in SEQ ID NO: 38; and

(22) FR1 as set forth in SEQ ID NO: 21, FR2 as set forth in SEQ ID NO: 32, FR3 as set forth in SEQ ID NO: 35 and FR4 as set forth in SEQ ID NO: 38.

According to the domain composition of a light chain variable region and a heavy chain variable region of an antibody known in the art, the light chain variable region or the heavy chain variable region of present antibody comprises the above domain components in an order of FR1-CDR1-FR2-CDR2-FR3-CDR3-FR4, or comprises the above domain components in an order of $(X)n$-FR1-$(X)n$-CDR1-$(X)n$-FR2-$(X)n$-CDR2-$(X)n$-FR3-$(X)n$-CDR3-$(X)n$-FR4-$(X)n$, in which, X is any amino acid residue, and n is zero or an integer greater than zero.

Preferably, the antibody provided by the present invention comprises a light chain variable region selected from the amino acid sequences shown in the following sequences:

SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57 and SEQ ID NO: 58;

and/or the antibody provided by the present invention comprises a heavy chain variable region selected from the amino acid sequences shown in the following sequences:

SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92 and SEQ ID NO: 93.

According to particular embodiments of the present invention, the antibody provided by the present invention comprises a combination of a light chain variable region and a heavy chain variable region selected from the group consisting of:

(1) a light chain variable region as set forth in SEQ ID NO: 57 and a heavy chain variable region as set forth in SEQ ID NO: 62;

(2) a light chain variable region as set forth in SEQ ID NO: 57 and a heavy chain variable region as set forth in SEQ ID NO: 63;

(3) a light chain variable region as set forth in SEQ ID NO: 57 and a heavy chain variable region as set forth in SEQ ID NO: 59;

(4) a light chain variable region as set forth in SEQ ID NO: 57 and a heavy chain variable region as set forth in SEQ ID NO: 60;

(5) a light chain variable region as set forth in SEQ ID NO: 57 and a heavy chain variable region as set forth in SEQ ID NO: 61;

(6) a light chain variable region as set forth in SEQ ID NO: 57 and a heavy chain variable region as set forth in SEQ ID NO: 67;

(7) a light chain variable region as set forth in SEQ ID NO: 57 and a heavy chain variable region as set forth in SEQ ID NO: 65;

(8) a light chain variable region as set forth in SEQ ID NO: 57 and a heavy chain variable region as set forth in SEQ ID NO: 66;

(9) a light chain variable region as set forth in SEQ ID NO: 57 and a heavy chain variable region as set forth in SEQ ID NO: 64;

(10) a light chain variable region as set forth in SEQ ID NO: 57 and a heavy chain variable region as set forth in SEQ ID NO: 68;

(11) a light chain variable region as set forth in SEQ ID NO: 57 and a heavy chain variable region as set forth in SEQ ID NO: 69;

(12) a light chain variable region as set forth in SEQ ID NO: 57 and a heavy chain variable region as set forth in SEQ ID NO: 70;

(13) a light chain variable region as set forth in SEQ ID NO: 57 and a heavy chain variable region as set forth in SEQ ID NO: 71;

(14) a light chain variable region as set forth in SEQ ID NO: 57 and a heavy chain variable region as set forth in SEQ ID NO: 72;

(15) a light chain variable region as set forth in SEQ ID NO: 57 and a heavy chain variable region as set forth in SEQ ID NO: 73;

(16) a light chain variable region as set forth in SEQ ID NO: 57 and a heavy chain variable region as set forth in SEQ ID NO: 89;

(17) a light chain variable region as set forth in SEQ ID NO: 57 and a heavy chain variable region as set forth in SEQ ID NO: 88;

(18) a light chain variable region as set forth in SEQ ID NO: 57 and a heavy chain variable region as set forth in SEQ ID NO: 87;

(19) a light chain variable region as set forth in SEQ ID NO: 57 and a heavy chain variable region as set forth in SEQ ID NO: 86;

(20) a light chain variable region as set forth in SEQ ID NO: 57 and a heavy chain variable region as set forth in SEQ ID NO: 83;

(21) a light chain variable region as set forth in SEQ ID NO: 57 and a heavy chain variable region as set forth in SEQ ID NO: 82;

(22) a light chain variable region as set forth in SEQ ID NO: 57 and a heavy chain variable region as set forth in SEQ ID NO: 81;

(23) a light chain variable region as set forth in SEQ ID NO: 57 and a heavy chain variable region as set forth in SEQ ID NO: 85;

(24) a light chain variable region as set forth in SEQ ID NO: 57 and a heavy chain variable region as set forth in SEQ ID NO: 84;

(25) a light chain variable region as set forth in SEQ ID NO: 57 and a heavy chain variable region as set forth in SEQ ID NO: 91;

(26) a light chain variable region as set forth in SEQ ID NO: 57 and a heavy chain variable region as set forth in SEQ ID NO: 90;

(27) a light chain variable region as set forth in SEQ ID NO: 57 and a heavy chain variable region as set forth in SEQ ID NO: 74;

(28) a light chain variable region as set forth in SEQ ID NO: 57 and a heavy chain variable region as set forth in SEQ ID NO: 75;

(29) a light chain variable region as set forth in SEQ ID NO: 57 and a heavy chain variable region as set forth in SEQ ID NO: 76;

(30) a light chain variable region as set forth in SEQ ID NO: 57 and a heavy chain variable region as set forth in SEQ ID NO: 77;

(31) a light chain variable region as set forth in SEQ ID NO: 57 and a heavy chain variable region as set forth in SEQ ID NO: 78;

(32) a light chain variable region as set forth in SEQ ID NO: 57 and a heavy chain variable region as set forth in SEQ ID NO: 80;

(33) a light chain variable region as set forth in SEQ ID NO: 39 and a heavy chain variable region as set forth in SEQ ID NO: 92;

(34) a light chain variable region as set forth in SEQ ID NO: 40 and a heavy chain variable region as set forth in SEQ ID NO: 92;

(35) a light chain variable region as set forth in SEQ ID NO: 41 and a heavy chain variable region as set forth in SEQ ID NO: 92;

(36) a light chain variable region as set forth in SEQ ID NO: 42 and a heavy chain variable region as set forth in SEQ ID NO: 92;

(37) a light chain variable region as set forth in SEQ ID NO: 43 and a heavy chain variable region as set forth in SEQ ID NO: 92;

(38) a light chain variable region as set forth in SEQ ID NO: 44 and a heavy chain variable region as set forth in SEQ ID NO: 92;

(39) a light chain variable region as set forth in SEQ ID NO: 44 and a heavy chain variable region as set forth in SEQ ID NO: 62;

(40) a light chain variable region as set forth in SEQ ID NO: 44 and a heavy chain variable region as set forth in SEQ ID NO: 68;

(41) a light chain variable region as set forth in SEQ ID NO: 44 and a heavy chain variable region as set forth in SEQ ID NO: 72;

(42) a light chain variable region as set forth in SEQ ID NO: 44 and a heavy chain variable region as set forth in SEQ ID NO: 82;

(43) a light chain variable region as set forth in SEQ ID NO: 44 and a heavy chain variable region as set forth in SEQ ID NO: 85;

(44) a light chain variable region as set forth in SEQ ID NO: 44 and a heavy chain variable region as set forth in SEQ ID NO: 91;

(45) a light chain variable region as set forth in SEQ ID NO: 48 and a heavy chain variable region as set forth in SEQ ID NO: 92;

(46) a light chain variable region as set forth in SEQ ID NO: 49 and a heavy chain variable region as set forth in SEQ ID NO: 92;

(47) a light chain variable region as set forth in SEQ ID NO: 50 and a heavy chain variable region as set forth in SEQ ID NO: 92;

(48) a light chain variable region as set forth in SEQ ID NO: 45 and a heavy chain variable region as set forth in SEQ ID NO: 92;

(49) a light chain variable region as set forth in SEQ ID NO: 46 and a heavy chain variable region as set forth in SEQ ID NO: 92;

(50) a light chain variable region as set forth in SEQ ID NO: 47 and a heavy chain variable region as set forth in SEQ ID NO: 92;

(51) a light chain variable region as set forth in SEQ ID NO: 56 and a heavy chain variable region as set forth in SEQ ID NO: 92;

(52) a light chain variable region as set forth in SEQ ID NO: 55 and a heavy chain variable region as set forth in SEQ ID NO: 92;

(53) a light chain variable region as set forth in SEQ ID NO: 55 and a heavy chain variable region as set forth in SEQ ID NO: 62;

(54) a light chain variable region as set forth in SEQ ID NO: 55 and a heavy chain variable region as set forth in SEQ ID NO: 68;

(55) a light chain variable region as set forth in SEQ ID NO: 55 and a heavy chain variable region as set forth in SEQ ID NO: 72;

(56) a light chain variable region as set forth in SEQ ID NO: 55 and a heavy chain variable region as set forth in SEQ ID NO: 82;

(57) a light chain variable region as set forth in SEQ ID NO: 55 and a heavy chain variable region as set forth in SEQ ID NO: 85;

(58) a light chain variable region as set forth in SEQ ID NO: 55 and a heavy chain variable region as set forth in SEQ ID NO: 91;

(59) a light chain variable region as set forth in SEQ ID NO: 54 and a heavy chain variable region as set forth in SEQ ID NO: 92;

(60) a light chain variable region as set forth in SEQ ID NO: 54 and a heavy chain variable region as set forth in SEQ ID NO: 62;

(61) a light chain variable region as set forth in SEQ ID NO: 54 and a heavy chain variable region as set forth in SEQ ID NO: 68;

(62) a light chain variable region as set forth in SEQ ID NO: 54 and a heavy chain variable region as set forth in SEQ ID NO: 72;

(63) a light chain variable region as set forth in SEQ ID NO: 54 and a heavy chain variable region as set forth in SEQ ID NO: 82;

(64) a light chain variable region as set forth in SEQ ID NO: 54 and a heavy chain variable region as set forth in SEQ ID NO: 85;

(65) a light chain variable region as set forth in SEQ ID NO: 54 and a heavy chain variable region as set forth in SEQ ID NO: 91;

(66) a light chain variable region as set forth in SEQ ID NO: 53 and a heavy chain variable region as set forth in SEQ ID NO: 92;

(67) a light chain variable region as set forth in SEQ ID NO: 51 and a heavy chain variable region as set forth in SEQ ID NO: 92;

(68) a light chain variable region as set forth in SEQ ID NO: 52 and a heavy chain variable region as set forth in SEQ ID NO: 92;

(69) a light chain variable region as set forth in SEQ ID NO: 52 and a heavy chain variable region as set forth in SEQ ID NO: 62;

(70) a light chain variable region as set forth in SEQ ID NO: 52 and a heavy chain variable region as set forth in SEQ ID NO: 91;

(71) a light chain variable region as set forth in SEQ ID NO: 58 and a heavy chain variable region as set forth in SEQ ID NO: 92;

(72) a light chain variable region as set forth in SEQ ID NO: 57 and a heavy chain variable region as set forth in SEQ ID NO: 93;

(73) a light chain variable region as set forth in SEQ ID NO: 44 and a heavy chain variable region as set forth in SEQ ID NO: 93;

(74) a light chain variable region as set forth in SEQ ID NO: 58 and a heavy chain variable region as set forth in SEQ ID NO: 91;

(75) a light chain variable region as set forth in SEQ ID NO: 55 and a heavy chain variable region as set forth in SEQ ID NO: 93; and

(76) a light chain variable region as set forth in SEQ ID NO: 51 and a heavy chain variable region as set forth in SEQ ID NO: 93.

The antibody provided by the present invention is capable of binding to IL-4R and functions as an antagonist of IL-4R. Preferably, the antibody is capable of binding to IL-4Rα, preferably to mammal IL-4Rα, more preferably to human IL-4Rα, even more preferably to human soluble IL-4Rα.

Binding affinity of the antibody provided by the present invention to IL-4Rα can be determined by method Biacore or ELISA. The antibody is determined to bind IL-4Rα with an affinity of less than 100 nM, less than 10 nM, less than 1 nM, less than 0.5 nM, and even less than 0.1 nM.

Under the same conditions, the ratio of the expression level of the antibody provided by the present invention to that of reference antibody is 0.1-3:1, preferably 0.3-3:1, more preferably 0.4-3:1, still preferably 0.5-3:1, still more preferably 0.6-3:1, further preferably 0.7-3:1, further more preferably 1-3:1.

In terms of antibody type, the antibody provided by the present invention can be a monoclonal antibody, fully or partially humanized antibody or chimeric antibody.

Or preferably, the antibody is an immunoglobulin, preferably IgA, IgD, IgE, IgG or IgM, more preferably IgG1, IgG2, IgG3 or IgG4 subtype, further more preferably IgG2 or IgG4 subtype.

In further another aspect, the invention provides a fusion protein or conjugate comprising the antibody of the present invention. The fusion protein or conjugate may further comprises cell surface receptor, active protein or active polypeptide, small molecule compound such as amino acid and saccharide, small molecule polymer or other parts chemically modifying the antibody, etc., bound to the present antibody by chemical or physical means.

In still another aspect, the present invention provides a nucleic acid sequence that can encode the heavy chain variable region and/or light chain variable region of the antibody provided by the present invention.

Preferably, the nucleic acid sequence can encode the heavy chain and/or light chain of the antibody provided by the present invention.

In yet another aspect, the present invention also provides a vector comprising the nucleic acid sequence provided by the present invention. The vector may be an eukaryotic expression vector, a prokaryotic expression vector, an artificial chromosome, a phage vector or the like.

The vector or nucleic acid sequence as described above can be used to transform or transfect host cells for purposes of preservation or antibody expression, and the like. Accordingly, the invention also provides a host cell transformed or transfected with the nucleic acid sequence or the vector. The host cell can be any prokaryotic or eukaryotic cell, such as a bacterial or insect, fungal, plant or animal cell.

The antibody provided by the present invention can be obtained through any method known in the art. For example, the heavy chain variable region and/or the light chain variable region of the antibody, or the heavy and/or light chain of the antibody can be obtained from the nucleic acid sequence provided by the present invention firstly, and then assembled into the antibody with any other domain of the antibody; or, the host cell provided by the present invention is cultured under conditions that the host cell is allowed to express the heavy chain variable region and/or the light chain variable region of the antibody or the heavy and/or light chain of the antibody for assembly into the antibody.

Optionally, the method further includes a step of recovering the produced antibody.

The antibody, fusion protein or conjugate, nucleic acid sequence, vector or host cell provided by the present invention or antibody produced by the method as described above may be contained in a pharmaceutical composition, and more particularly, in a pharmaceutical preparation for various purposes as actually needed. Therefore, in a further aspect, the present invention also provides a pharmaceutical composition comprising the antibody, fusion protein or conjugate, nucleic acid sequence, vector, host cell of the present invention and/or antibody produced by the method as described above.

Optionally, the pharmaceutical composition can be a pharmaceutical preparation. The pharmaceutical preparation is, for example, an injection.

The pharmaceutical composition or pharmaceutical preparation may further comprises a pharmaceutically acceptable carrier or excipient, depending on the particular dosage form.

In the pharmaceutical composition or pharmaceutical preparation, at least one of the following medicaments may also be contained: antiasthmatics such as albuterol etc., antihistamines such as loratadine etc., Immunosuppressive agents such as tacrolimus and pimecrolimus etc., M receptor blockers such as ipratropium bromide etc., leukotriene receptor blockers such as montelukast etc., phosphodiesterase inhibitors such as theophylline etc., non-steroidal anti-inflammatory drugs such as 5-aminosalicylic acid etc., hormones such as beclomethasone and budesonide etc., that is to say the antibody, fusion protein or conjugate, nucleic acid sequence, vector, host cell provided by the preset invention or antibody produced by the present method as described above may be used in combination with other medicaments as required.

In still further another aspect, the present invention also provides use of the antibody, fusion protein or conjugate, nucleic acid sequence, vector, host cell or antibody produced by the method for manufacturing a medicament for the prevention, treatment or amelioration of inflammation or allergic disease.

Preferably, the inflammation or allergic disease includes autoimmune disease, such as allergic dermatitis, asthma, eosinophilic esophagitis, eczema, allergic rhinitis, nasal polyp, rheumatoid arthritis and the like.

In still yet another aspect, the present invention provides a method of preventing, treating or ameliorating inflammation or allergic disease, and the method includes administering to a subject in need thereof the antibody, fusion protein or conjugate, nucleic acid sequence, vector, host cell provided by the present invention and/or antibody produced by the present method.

Preferably, the subject is a mammal, more preferably, the subject is a human.

Preferably, the inflammation or allergic disease includes autoimmune disease, such as allergic dermatitis, asthma, eosinophilic esophagitis, eczema, allergic rhinitis, nasal polyp, rheumatoid arthritis and the like.

Other medicaments can be used in combination to prevent, treat or ameliorate inflammation or allergic disease, for example, the method further includes administering to a subject in need thereof at least one medicament selected from the group consisting of: antiasthmatics such as albuterol etc., antihistamines such as loratadine etc., Immunosuppressive agents such as tacrolimus and pimecrolimus etc., M receptor blockers such as ipratropium bromide etc., leukotriene receptor blockers such as montelukast etc., phosphodiesterase inhibitors such as theophylline etc., non-steroidal anti-inflammatory drugs such as 5-aminosalicylic acid, etc., hormones such as beclomethasone and budesonide etc.

Preferably, the medicament is administered simultaneously or sequentially with the antibody, fusion protein or conjugate, nucleic acid sequence, vector, host cell provided by the present invention and/or antibody produced by the present method.

In further yet another aspect, the present invention also provides a kit, and the kit comprises the antibody, fusion protein or conjugate, nucleic acid sequence, vector, host cell provided by the present invention and/or antibody produced by the present method.

BRIEF DESCRIPTION OF THE DRAWINGS

The invention may be better understood by combination with the non-limiting embodiments of the present invention and the accompanying drawings, in which.

DETAILED DESCRIPTION OF PREFERRED EMBODIMENTS

Figure 1:
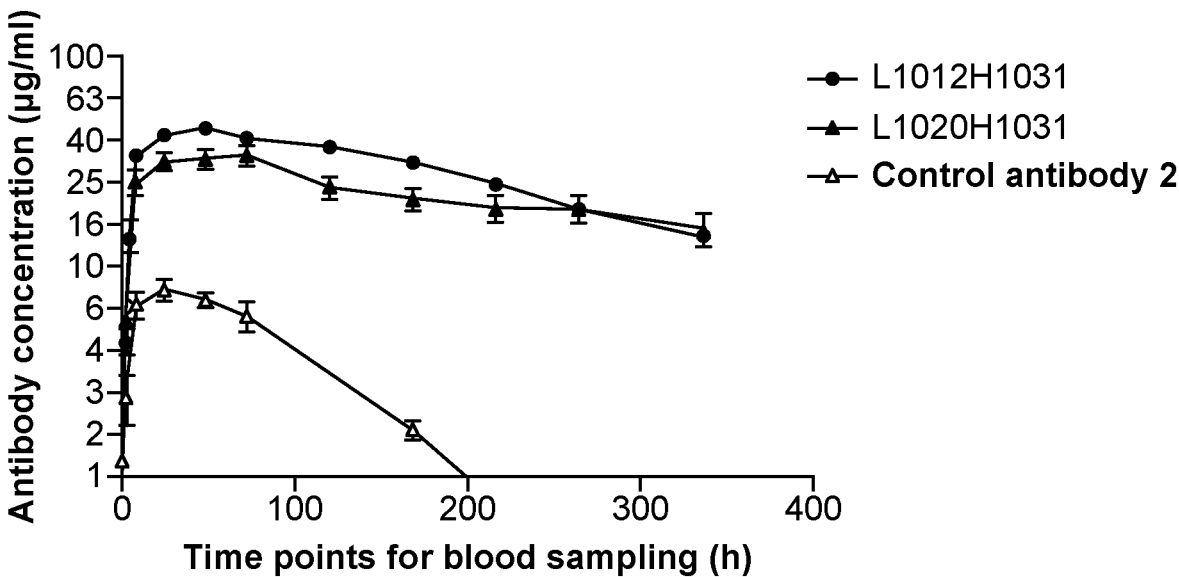
FIG. 1 shows the pharmacokinetic curves of the antibodies of the present invention in mouse.

The present invention will be further described in detail in combination with the particular embodiments hereinafter. It will be appreciated by those skilled in the art that the embodiments provided are only used to illustrate the present invention, rather than limiting the scope of the present invention in any way.

Experimental methods in the following Examples are all conventional methods, unless particularly stated. Raw materials used in the following Examples are commercially available from conventional biochemical reagent stores, unless particularly stated.

In the following Examples, the antibodies shown in Table 1 and their effects are exemplarily provided and verified.

TABLE 1

Exemplary antibodies provided by the present invention

| Number | SED ID NOs of the light chain variable region and the heavy chain variable region |
|---|---|
| L1000H1007 | SEQ ID NO:: 57 + SEQ ID NO:: 62 |
| L1000H1008 | SEQ ID NO:: 57 + SEQ ID NO:: 63 |
| L1000H1009 | SEQ ID NO:: 57 + SEQ ID NO: 59 |
| L1000H1010 | SEQ ID NO: 57 + SEQ ID NO: 60 |
| L1000H1011 | SEQ ID NO: 57 + SEQ ID NO: 61 |
| L1000H1012 | SEQ ID NO: 57 + SEQ ID NO: 67 |
| L1000H1013 | SEQ ID NO: 57 + SEQ ID NO: 65 |
| L1000H1014 | SEQ ID NO: 57 + SEQ ID NO: 66 |
| L1000H1015 | SEQ ID NO: 57 + SEQ ID NO: 64 |
| L1000H1016 | SEQ ID NO: 57 + SEQ ID NO: 68 |
| L1000H1017 | SEQ ID NO: 57 + SEQ ID NO: 69 |
| L1000H1018 | SEQ ID NO: 57 + SEQ ID NO: 70 |
| L1000H1019 | SEQ ID NO: 57 + SEQ ID NO: 71 |
| L1000H1020 | SEQ ID NO: 57 + SEQ ID NO: 72 |
| L1000H1021 | SEQ ID NO: 57 + SEQ ID NO: 73 |
| L1000H1022 | SEQ ID NO: 57 + SEQ ID NO: 89 |
| L1000H1023 | SEQ ID NO: 57 + SEQ ID NO: 88 |
| L1000H1024 | SEQ ID NO: 57 + SEQ ID NO: 87 |
| L1000H1025 | SEQ ID NO: 57 + SEQ ID NO: 86 |
| L1000H1026 | SEQ ID NO: 57 + SEQ ID NO: 83 |
| L1000H1027 | SEQ ID NO: 57 + SEQ ID NO: 82 |
| L1000H1028 | SEQ ID NO: 57 + SEQ ID NO: 81 |
| L1000H1029 | SEQ ID NO: 57 + SEQ ID NO: 85 |
| L1000H1030 | SEQ ID NO: 57 + SEQ ID NO: 84 |
| L1000H1031 | SEQ ID NO: 57 + SEQ ID NO: 91 |
| L1000H1032 | SEQ ID NO: 57 + SEQ ID NO: 90 |
| L1000H1033 | SEQ ID NO: 57 + SEQ ID NO: 74 |
| L1000H1034 | SEQ ID NO: 57 + SEQ ID NO: 75 |
| L1000H1035 | SEQ ID NO: 57 + SEQ ID NO: 76 |
| L1000H1036 | SEQ ID NO: 57 + SEQ ID NO: 77 |
| L1000H1037 | SEQ ID NO: 57 + SEQ ID NO: 78 |
| L1000H1038 | SEQ ID NO: 57 + SEQ ID NO: 80 |
| L1007H1000 | SEQ ID NO: 39 + SEQ ID NO: 92 |
| L1008H1000 | SEQ ID NO: 40 + SEQ ID NO: 92 |
| L1009H1000 | SEQ ID NO: 41 + SEQ ID NO: 92 |
| L1010H1000 | SEQ ID NO: 42 + SEQ ID NO: 92 |
| L1011H1000 | SEQ ID NO: 43 + SEQ ID NO: 92 |
| L1012H1000 | SEQ ID NO: 44 + SEQ ID NO: 92 |
| L1012H1007 | SEQ ID NO: 44 + SEQ ID NO: 62 |
| L1012H1016 | SEQ ID NO: 44 + SEQ ID NO: 68 |
| L1012H1020 | SEQ ID NO: 44 + SEQ ID NO: 72 |
| L1012H1027 | SEQ ID NO: 44 + SEQ ID NO: 82 |
| L1012H1029 | SEQ ID NO: 44 + SEQ ID NO: 85 |
| L1012H1031 | SEQ ID NO: 44 + SEQ ID NO: 91 |
| L1013H1000 | SEQ ID NO: 48 + SEQ ID NO: 92 |
| L1014H1000 | SEQ ID NO: 49 + SEQ ID NO: 92 |
| L1015H1000 | SEQ ID NO: 50 + SEQ ID NO: 92 |
| L1016H1000 | SEQ ID NO: 45 + SEQ ID NO: 92 |
| L1017H1000 | SEQ ID NO: 46 + SEQ ID NO: 92 |
| L1018H1000 | SEQ ID NO: 47 + SEQ ID NO: 92 |
| L1019H1000 | SEQ ID NO: 56 + SEQ ID NO: 92 |
| L1020H1000 | SEQ ID NO: 55 + SEQ ID NO: 92 |
| L1020H1007 | SEQ ID NO: 55 + SEQ ID NO: 62 |
| L1020H1016 | SEQ ID NO: 55 + SEQ ID NO: 68 |
| L1020H1020 | SEQ ID NO: 55 + SEQ ID NO: 72 |
| L1020H1027 | SEQ ID NO: 55 + SEQ ID NO: 82 |
| L1020H1029 | SEQ ID NO: 55 + SEQ ID NO: 85 |
| L1020H1031 | SEQ ID NO: 55 + SEQ ID NO: 91 |
| L1021H1000 | SEQ ID NO: 54 + SEQ ID NO: 92 |
| L1021H1007 | SEQ ID NO: 54 + SEQ ID NO: 62 |
| L1021H1016 | SEQ ID NO: 54 + SEQ ID NO: 68 |

TABLE 1-continued

Exemplary antibodies provided by the present invention

| Number | SED ID NOs of the light chain variable region and the heavy chain variable region |
|---|---|
| L1021H1020 | SEQ ID NO: 54 + SEQ ID NO: 72 |
| L1021H1027 | SEQ ID NO: 54 + SEQ ID NO: 82 |
| L1021H1029 | SEQ ID NO: 54 + SEQ ID NO: 85 |
| L1021H1031 | SEQ ID NO: 54 + SEQ ID NO: 91 |
| L1022H1000 | SEQ ID NO: 53 + SEQ ID NO: 92 |
| L1023H1000 | SEQ ID NO: 51 + SEQ ID NO: 92 |
| L1024H1000 | SEQ ID NO: 52 + SEQ ID NO: 92 |
| L1024H1007 | SEQ ID NO: 52 + SEQ ID NO: 62 |
| L1024H1031 | SEQ ID NO: 52 + SEQ ID NO: 91 |
| L1001H1000 | SEQ ID NO: 58 + SEQ ID NO: 92 |
| L1000H1001 | SEQ ID NO: 57 + SEQ ID NO: 93 |
| L1012H1001 | SEQ ID NO: 44 + SEQ ID NO: 93 |
| L1001H1031 | SEQ ID NO: 58 + SEQ ID NO: 91 |
| L1020H1001 | SEQ ID NO: 55 + SEQ ID NO: 93 |
| L1023H1001 | SEQ ID NO: 51 + SEQ ID NO: 93 |
| L1000H1000 | SEQ ID NO: 57 + SEQ ID NO: 92 |
| L1001H1001 | SEQ ID NO: 58 + SEQ ID NO: 93 |

Example 1: Preparation of the Antibodies of the Present Invention and Determination of Expression Levels by Non-Reduced SDS-PAGE Gel Electrophoresis The sequence coding for the light chain variable region of the antibody was inserted into vector pFUSE2ss-CLIg-hK (Invivogen, Catalog Number: pfuse2ss-hclk) using EcoRI and BsiWI restriction sites to construct a light chain expression vector.

The sequence coding for the heavy chain variable region of the antibody was inserted into vector pFUSEss-CHIg-hG2 (Invivogen, Catalog Number: pfusess-hchg2) or vector pFUSEss-CHIg-hG4 (Invivogen, Catalog Number: pfusess-hchg4) using EcoRI and NheI restriction sites to construct a heavy chain expression vector.

The culture and transfection of Expi293 cells were performed in accordance with the handbook of Expi293™ Expression System Kit from Invitrogen (Catalog Number: A14635). The density of the cells was adjusted to $2 \times 10^6$ cells/ml for transfection, and 0.6 μg of the light chain expression vector as described above and 0.4 μg of the heavy chain expression vector as described above were added to each ml of cell culture, and the supernatant of the culture was collected four days later.

The culture supernatant was subjected to non-reduced SDS-PAGE gel electrophoresis in accordance with the protocol described in Appendix 8, the Third edition of the "Molecular Cloning: A Laboratory Manual".

Pictures were taken with a gel scanning imaging system from BEIJING JUNYI Electrophoresis Co., LTD and in-gel quantification was performed using Gel-PRO ANALYZER software to determine the expression levels of the antibodies after transient transfection. Results were expressed relative to the expression level of control antibody 1 (control antibody 1 was constructed according to U.S. Pat. No. 7,186, 809, which comprises a light chain variable region as set forth in SEQ ID NO: 10 of U.S. Pat. No. 7,186,809 and a heavy chain variable region as set forth in SEQ ID NO: 12 of U.S. Pat. No. 7,186,809, the same below) (control antibody 2 was constructed according to U.S. Pat. No. 7,638, 606, which comprises a light chain variable region as set forth in SEQ ID NO: 6 of U.S. Pat. No. 7,638,606 and a variable region as set forth in SEQ ID NO: 42 of U.S. Pat. No. 7,638,606, the same below). See Tables 2a-2c below for the results.

TABLE 2a

Expression levels of the antibodies of the present
invention after transient transfection (antibodies whose
expression levels are significantly higher than that of control antibody 1):

| Number of the antibody | Expression level vs control antibody 1 | Number of the antibody | Expression level vs control antibody 1 |
|---|---|---|---|
| L1021H1000 | 2.08 | L1000H1028 | 1.27 |
| L1020H1000 | 1.58 | L1000H1015 | 1.19 |
| L1000H1027 | 1.56 | L1000H1032 | 1.18 |
| L1000H1024 | 1.51 | L1000H1026 | 1.15 |
| L1000H1025 | 1.48 | L1021H1029 | 1.12 |
| L1001H1000 | 1.48 | L1000H1030 | 1.1 |
| L1021H1016 | 1.43 | L1024H1031 | 1.08 |
| L1000H1014 | 1.35 | L1000H1016 | 1.05 |

TABLE 2b

Expression levels of the antibodies of the present
invention after transient transfection (antibodies whose
expression levels are slightly lower than that of control antibody 1):

| Number of the antibody | Expression level vs control antibody 1 | Number of the antibody | Expression level vs control antibody 1 |
|---|---|---|---|
| L1000H1031 | 0.99 | L1017H1000 | 0.85 |
| L1021H1031 | 0.99 | L1020H1016 | 0.84 |
| L1020H1029 | 0.96 | L1000H1009 | 0.81 |
| control antibody 2 | 0.93 | L1000H1007 | 0.8 |
| L1012H1000 | 0.89 | L1000H1023 | 0.8 |
| L1019H1000 | 0.87 | L1020H1027 | 0.78 |
| L1020H1031 | 0.87 | L1024H1007 | 0.77 |
| L1021H1020 | 0.87 | L1000H1013 | 0.75 |
| L1000H1029 | 0.86 | L1020H1007 | 0.74 |
| L1008H1000 | 0.86 | L1021H1007 | 0.74 |
| L1000H1001 | 0.85 | L1000H1021 | 0.71 |

TABLE 2c

Expression levels of the antibodies of the present
invention after transient transfection (antibodies whose
expression levels are significantly lower than that of control antibody 1):

| Number of the antibody | Expression level vs control antibody 1 | Number of the antibody | Expression level vs control antibody 1 |
|---|---|---|---|
| L1000H1020 | 0.69 | L1024H1000 | 0.52 |
| L1010H1000 | 0.69 | L1000H1008 | 0.51 |
| L1000H1022 | 0.67 | L1000H1037 | 0.5 |
| L1000H1012 | 0.64 | L1007H1000 | 0.49 |
| L1022H1000 | 0.64 | L1016H1000 | 0.49 |
| L1011H1000 | 0.63 | L1000H1017 | 0.47 |
| L1000H1011 | 0.62 | L1000H1035 | 0.46 |
| L1000H1033 | 0.62 | L1012H1027 | 0.46 |
| L1020H1020 | 0.61 | L1018H1000 | 0.44 |
| L1000H1036 | 0.6 | L1023H1000 | 0.43 |
| L1021H1027 | 0.6 | L1012H1016 | 0.42 |
| L1012H1007 | 0.59 | L1013H1000 | 0.41 |
| L1009H1000 | 0.57 | L1000H1034 | 0.4 |
| L1012H1020 | 0.57 | L1000H1018 | 0.35 |
| L1012H1031 | 0.56 | L1000H1019 | 0.34 |
| L1000H1038 | 0.54 | L1015H1000 | 0.27 |
| L1012H1029 | 0.54 | L1014H1000 | 0.17 |
| L1000H1010 | 0.53 | | |

Example 2: Detection of Inhibitory Effect of the
Antibodies of the Present Invention on Proliferation
of TF-1 Cells by hIL-4 or hIL-13

1. Preparation of Reagents hIL-4 (Invivogen, Catalog Number: rhiI-4) solution: hIL-4 was dissolved in 100 μl of PBS containing 0.1% BSA (Beyotime, Catalog Number: ST023) to obtain a solution with a concentration of 100 μg/ml, and the dissolved hIL-4 was dispensed into 1.5 ml (Nunc) centrifuge tubes in a volume of 5 μl per tube, and then the tubes were stored in a refrigerator at −20° C.

WST-1 (Beyotime, Catalog Number: 00036) solution: 5 ml of electron coupling agent (C0036-2) was added to WST-1 powder (C0036-1), and the WST-1 solution was obtained when the WST-1 powder was dissolved completely, then dispensed into 1.5 ml (Nunc) centrifuge tubes in a volume of 620 μl per tube, and then the tubes were stored in a refrigerator at −20° C.

2. Culture of TF-1 Cells

TF-1 cells (ATCC: CRL-2003™) frozen in liquid nitrogen were taken out, shaken in a 37° C. water bath to dissolve quickly. The dissolved cell suspension was transferred to a 15 ml centrifuge tube, and then 1640 medium was added therein to 10 ml. The tube was centrifuged at 800 rpm for 5 min, the supernatant therein was aspirated, and cell pellets were retained and washed once again. 10 ml of 1640 medium containing 10% FBS and 2 ng/ml GM-CSF (Sino Biological, Catalog Number: 10015-H01H) was added to the tube, and a cell density of $1 \times 10^5 - 1 \times 10^6$ cells/ml was obtained. The suspension was transferred to a T75 cell culture flask (Nunc), and the cells were statically cultured in an incubator (Thermo) at 37° C., 5% $CO_2$. Every 2-3 days, the cell suspension was taken out, centrifuged at 800 rpm for 5 min, and the cells were resuspended in 10 ml of medium. Subsequently, $1 \times 10^6$ cells were counted and transferred into a new T75 cell culture flask, and the medium was supplemented thereto to 10 ml. The cells were continuously passaged for 2-3 times to reach a good state (the cells were bright and had a slightly irregular shape when suspended individually) for proliferation blocking experiment.

3. Preparation and Purification of the Antibodies a) Cell culture supernatant samples of the antibodies of the present invention:

Expi293 cells were transfected with plasmids carrying different groups of genes of the antibodies, and 200 μl of the cell culture supernatant was taken out 4 days after transfection, and then centrifuged at 800 rpm for 5 min. The supernatant was filtered through a 0.22 μm pore size filter and used for proliferation blocking experiment.

b) Purified antibody samples of the present invention: For each antibody of the present invention, the culture supernatant of cells expressing the antibody was passed through a 0.22 μm filter and then purified by GE MabSelect Sure (Catalog Number: 11003494) Protein A affinity chromatography column in a purification system GE AKTA purifier 10. The purified antibody was collected and concentrated using Amicon ultrafiltration concentrator (Catalog Number: UFC903096) and then quantified. The antibody was diluted with PBS to 0 to 1 μg/ml for the proliferation blocking experiment.

4. Proliferation Blocking Experiment

The well-grown cells in the T75 cell flask were taken out and transferred into a 15 ml centrifuge tube, which was then centrifuged at 800 rpm for 5 min. The supernatant was discarded and the cell pellets were resuspended with 10 ml PBS, centrifuged at 800 rpm for 5 min. The supernatant was discarded and the cell pellets were resuspended in 10 ml of 1640 medium (without GM-CSF) containing 10% FBS, centrifuged at 800 rpm for 5 min. The supernatant was discarded and the cell pellets were resuspended in 5 ml of 1640 medium (without GM-CSF) containing 10% FBS. The cells were counted and adjusted to a cell density of $5 \times 10^5$ cells/ml through supplementing the medium. The cell suspension was added to a 96-well plate at a volume of 80 μl per well (wells in the outer ring were left free of cells to prevent volatilization). For each antibody of the present invention, 10 μl of purified antibody with different concentrations or 10 μl of the corresponding cell culture supernatant was added to the cells in the 96-well plate (in 3 replicate wells). The hIL-4 was then diluted to 50 ng/ml with 1640 medium containing 10% FBS, and was added to the corresponding wells in the 96-well plate in a volume of 10 μl per well, so that the final cell density was $4 \times 10^5$ cells/ml, the concentration of hIL-4 was 5 ng/ml, and the volume in each well of the 96-well plate was 100 μl. A negative control group (in 3 replicate wells) was set, in which no hIL-4 or the antibody was added, and only the same number of cells and the same volume of the culture medium were added. Meanwhile, a positive control group (in 3 replicate wells) with addition of the same concentration of hIL-4 and the same volume of the medium was set, and no antibody was added in in this group. 200 μl of PBS was added to each well in the outer ring of the 96-well cell plate to prevent the volatilization of liquid in the inner ring. The 96-well cell plate was placed in a 5% $CO_2$ incubator at 37° C. for static culture.

The above experiment was repeated with the same procedure using 500 ng/ml of hIL-13 (its final concentration was 50 ng/ml after being added into the cells).

5. Data Statistics

After the 96-well cell plates were statically cultured for 72 hours in the 5% $CO_2$ incubator, 10 μl of the WST-1 solution was added to the cells in each well. The 96-well cell plate was placed in a 5% $CO_2$ incubator at 37° C. for further static culture. 24 h later, the 96-well plate was placed in flexstation 3 (Molecular Devices) and the values of OD450-OD650 were read.

For the culture supernatants of the antibodies of the invention, the values of OD450-OD650 (OD value) of them and those of the positive control group and the negative control group were used to calculate inhibitory rate as follows: inhibitory rate=(OD value of supernatant of the transfected cells−OD value of the positive control group)/ (OD value of the negative control group−OD value of the positive control group)×100%. The results of blocking effect of the antibodies of the present invention on the proliferation of TF-1 cells by hIL-4 or hIL-13 are shown in Tables 3a-3b below.

For the purified antibodies of the present invention with different concentrations, the measured OD450-OD650 data were input into prism5 software, in which the value of the negative control group was set to the lowest one, the value of the positive control group was set to the highest one, and the logarithm of the antibody concentration was taken. Then the curve of the antibody concentration logarithm to the OD450-OD650 value was fitted by prism5 software. The calculated IC50s are shown in Table 4 below.

TABLE 3a

Screening results of inhibitory effects of the antibodies of the present invention on the proliferation activity of TF-1 cells (antibodies with increased inhibitory rates compared with control antibody 1).

| Number of the antibody | Inhibitory rate on pro-proliferative effect of IL-4 | Inhibitory rate on pro-proliferative effect of IL-13 |
| --- | --- | --- |
| control antibody 1 | 0.87 | 0.63 |
| control antibody 2 | 1 | 0.87 |
| L1020H1029 | 1.03 | 0.93 |

TABLE 3a-continued

Screening results of inhibitory effects of the antibodies of the present invention on the proliferation activity of TF-1 cells (antibodies with increased inhibitory rates compared with control antibody 1).

| Number of the antibody | Inhibitory rate on pro-proliferative effect of IL-4 | Inhibitory rate on pro-proliferative effect of IL-13 |
| --- | --- | --- |
| L1000H1001 | 1.03 | 0.93 |
| L1021H1027 | 1.02 | 0.94 |
| L1020H1027 | 1.02 | 0.92 |
| L1021H1029 | 1.02 | 0.92 |
| L1020H1016 | 1.01 | 0.97 |
| L1024H1031 | 1.01 | 0.94 |
| L1021H1031 | 1.01 | 0.93 |
| L1020H1031 | 1.01 | 0.93 |
| L1000H1029 | 1.01 | 0.92 |
| L1000H1027 | 1.01 | 0.86 |
| L1021H1016 | 1 | 0.94 |
| L1021H1007 | 1 | 0.86 |
| L1000H1028 | 1 | 0.84 |
| L1000H1014 | 0.99 | 0.78 |
| L1001H1000 | 0.98 | 0.85 |
| L1000H1024 | 0.98 | 0.75 |
| L1000H1031 | 0.97 | 0.83 |
| L1000H1007 | 0.96 | 0.82 |
| L1000H1023 | 0.96 | 0.8 |
| L1000H1032 | 0.96 | 0.74 |
| L1020H1007 | 0.95 | 0.9 |
| L1021H1000 | 0.95 | 0.78 |
| L1000H1016 | 0.95 | 0.76 |
| L1012H1029 | 0.94 | 0.95 |
| L1012H1007 | 0.93 | 0.88 |
| L1021H1020 | 0.91 | 0.75 |
| L1020H1000 | 0.91 | 0.7 |
| L1000H1025 | 0.91 | 0.69 |
| L1012H1020 | 0.9 | 0.78 |
| L1000H1020 | 0.88 | 0.76 |
| L1000H1012 | 0.88 | 0.58 |
| L1020H1020 | 0.87 | 0.76 |

TABLE 3b

Screening results of inhibitory effects of the antibodies of the present invention on the proliferation activity of TF-1 cells (antibodies with the same or decreased inhibitory rates compared with control antibody 1).

| Number of the antibody | Inhibitory rate on pro-proliferative effect of IL-4 | Inhibitory rate on pro-proliferative effect of IL-13 |
| --- | --- | --- |
| L1000H1022 | 0.87 | 0.62 |
| L1000H1017 | 0.87 | 0.59 |
| L1000H1030 | 0.87 | 0.47 |
| L1024H1007 | 0.86 | 0.7 |
| L1000H1013 | 0.86 | 0.55 |
| L1012H1031 | 0.85 | 0.7 |
| L1000H1015 | 0.85 | 0.63 |
| L1000H1026 | 0.85 | 0.53 |
| L1000H1018 | 0.84 | 0.65 |
| L1000H1009 | 0.83 | 0.54 |
| L1012H1000 | 0.78 | 0.5 |
| L1012H1016 | 0.78 | 0.48 |
| L1000H1021 | 0.73 | 0.56 |
| L1019H1000 | 0.72 | 0.49 |
| L1008H1000 | 0.67 | 0.27 |
| L1009H1000 | 0.66 | 0.35 |
| L1000H1008 | 0.66 | 0.19 |
| L1012H1027 | 0.65 | 0.63 |
| L1000H1011 | 0.61 | 0.26 |
| L1000H1010 | 0.54 | 0.1 |
| L1000H1019 | 0.52 | 0.29 |
| L1007H1000 | 0.49 | 0.15 |
| L1024H1000 | 0.44 | 0.39 |
| L1011H1000 | 0.44 | 0.13 |
| L1017H1000 | 0.44 | 0.02 |
| L1018H1000 | 0.42 | −0.12 |

TABLE 3b-continued

Screening results of inhibitory effects of the antibodies of the present
invention on the proliferation activity of TF-1 cells (antibodies with
the same or decreased inhibitory rates compared with control antibody 1).

| Number of the antibody | Inhibitory rate on pro-proliferative effect of IL-4 | Inhibitory rate on pro-proliferative effect of IL-13 |
|---|---|---|
| L1010H1000 | 0.38 | 0.06 |
| L1000H1036 | 0.27 | 0.18 |
| L1023H1000 | 0.26 | 0.07 |
| L1000H1033 | 0.23 | 0.14 |
| L1015H1000 | 0.16 | 0.09 |
| L1000H1034 | 0.15 | 0.1 |
| L1016H1000 | 0.1 | −0.36 |
| L1013H1000 | 0.01 | −0.21 |
| L1022H1000 | −0.05 | 0.02 |
| L1000H1038 | −0.05 | −0.15 |
| L1014H1000 | −0.05 | −0.29 |
| L1000H1037 | −0.06 | −0.13 |
| L1000H1035 | −0.12 | −0.13 |

TABLE 4

Activity data of the purified antibodies
(600-900 ml) after transient transfection

| | IC50 (ng/ml) (Inhibition on the proliferation of IL-4) | IC50 (ng/ml) (Inhibition on the proliferation of IL-13) |
|---|---|---|
| control antibody 1 | 184.03 ± 61.95 | 345.1 ± 73.9 |
| control antibody 2 | 27.79 ± 3.22 | 52.06 ± 14.97 |
| L1021H1016 | 28.46 ± 7.82 | 69.67 ± 28.38 |
| L1021H1020 | 15.36 ± 2.46 | 28.64 ± 10.46 |
| L1021H1031 | 34.27 ± 12.17 | 76.51 ± 31.94 |
| L1020H1016 | 24.19 ± 6.91 | 44.62 ± 14.79 |
| L1020H1020 | 23.63 ± 8.73 | 53.73 ± 17.34 |
| L1020H1031 | 25.6 ± 7.46 | 60.17 ± 19.02 |
| L1012H1016 | 32.44 ± 7.45 | 75.33 ± 43.63 |
| L1012H1020 | 21.09 ± 4.72 | 56.65 ± 23.34 |
| L1012H1031 | 39.26 ± 15.61 | 76.87 ± 40.97 |

Example 3 Detection of the Binding Abilities of the Antibodies of the Present Invention to sIL-4Rα by ELISA 1. Preparation of Reagents sIL-4Rα (PEPRO TECH, Catalog Number: 200-04R) solution: the sIL-4Rα was taken and 1 ml ddH2O was added therein, mixed up and down, and then a solution of 100 µg/ml was obtained. The solution was stored in a refrigerator at −20° C. after being subpacked.

Sample to be tested: For each antibody of the present invention, 10 µl and 2 µl of the culture supernatant of Expi293 cells expressing the antibody after transient transfection (the medium was Expi293 Expression Medium, Invitrogen, Catalog Number: A1435102; suspension culture was performed for 4 days at 100 rpm in a 8% CO2 incubator) were respectively added to 990 µl and 998 µl of PBS to prepare antibody samples to be tested of 1:100 and 1:500 dilutions.

Control sample: As negative control samples, the culture supernatant of normal cells (untransfected Expi293 cells; the medium was Expi293 Expression Medium, Invitrogen, Catalog Number: A1435102; suspension culture was performed for 4 days at 100 rpm in a 8% CO2 incubator) were also diluted at 1:100 and 1:500.

2. Detection by ELISA

100 µl of 100 µg/ml sIL-4Rα solution was added to 9.90 ml of PBS, mixed up and down, and then an antigen coating buffer of 1.0 µg/ml was obtained. The prepared antigen coating buffer was added to a 96-well ELISA plate (Corning) with a volume of 100 µl per well. The 96-well ELISA plate was incubated overnight in a refrigerator at 4° C. On the next day, the solution therein was discarded, and PBS containing 2% BSA was added to the 96-well ELISA plate row by row with a volume of 300 µl per well. The 96-well ELISA plate was incubated for 2 hours in a refrigerator at 4° C. Then the PBS containing 2% BSA was discarded and the plate was washed 3 times with PBST. Diluted antibodies to be tested were sequentially added to the corresponding wells, while the normal cell culture supernatants, as negative control samples, were added too. Three duplicate wells were made for each sample with a volume of 100 µl per well. The ELISA plate was wrapped with preservative film (or covered) and incubated for 1 h at 10° C. in a constant temperature incubator. Subsequently, the 96-well ELISA plate was taken out, and the solution therein was discarded. After washing with PBST for 3 times, TMB solution (Solarbio, Catalog Number: PR1200) was added to the 96-well ELISA plate row by row with a volume of 100 µl per well. The 96-well ELISA plate was placed at room temperature for 5 minutes, and 2 M H2SO4 solution was added in immediately to terminate the reaction. The 96-well ELISA plate was placed in flexstation 3 (Molecular Devices), the values of OD450 were read, and the data were collected, calculated and analyzed. Results were expressed relative to the affinity of control antibody 1. See Tables 5a-5c below for the results.

TABLE 5a

The affinities of the antibodies of the present
invention for sIL-4Rα (antibodies whose affinities are
significantly greater than that of control antibody 1)

| Number of the antibody | OD 450/ OD450$_{Control\ antibody\ 1}$ |
|---|---|
| Control antibody 1 | 1 |
| L1021H1000 | 2.42 |
| L1020H1000 | 2.27 |
| L1019H1000 | 1.79 |
| L1001H1000 | 1.56 |
| L1012H1000 | 1.22 |
| L1000H1031 | 1.14 |
| L1020H1031 | 1.12 |
| L1000H1014 | 1.06 |
| L1020H1029 | 1.01 |

TABLE 5b

The affinities of the antibodies of the present
invention for sIL-4Rα (antibodies whose affinities are
equal to or slightly lower than that of control antibody 1)

| Number of the antibody | OD 450/ OD450$_{Control\ antibody\ 1}$ |
|---|---|
| L1010H1000 | 1 |
| L1021H1029 | 1 |
| L1011H1000 | 0.9 |
| L1008H1000 | 0.9 |
| L1021H1031 | 0.9 |
| L1024H1031 | 0.9 |
| L1007H1000 | 0.8 |
| L1020H1016 | 0.8 |
| L1000H1029 | 0.8 |
| L1000H1001 | 0.7 |

TABLE 5c

The affinities of the antibodies of the present
invention for sIL-4Rα (antibodies whose affinities
significantly lower than that of control antibody 1)

| Number of the antibody | OD 450/ OD450$_{Control\ antibody\ 1}$ |
|---|---|
| L1024H1000 | 0.69 |
| L1015H1000 | 0.67 |
| L1000H1015 | 0.65 |
| L1009H1000 | 0.64 |
| L1021H1016 | 0.63 |
| L1000H1023 | 0.63 |
| L1000H1016 | 0.61 |
| L1000H1009 | 0.56 |
| L1000H1032 | 0.53 |
| L1017H1000 | 0.49 |
| L1021H1007 | 0.44 |
| L1000H1027 | 0.44 |
| L1020H1007 | 0.40 |
| L1020H1027 | 0.40 |
| L1012H1007 | 0.40 |
| L1000H1013 | 0.38 |
| L1000H1007 | 0.37 |
| L1000H1021 | 0.35 |
| L1000H1028 | 0.33 |
| L1021H1027 | 0.29 |
| L1016H1000 | 0.27 |
| L1020H1020 | 0.26 |
| L1000H1024 | 0.26 |
| L1021H1020 | 0.24 |
| L1013H1000 | 0.24 |
| L1024H1007 | 0.23 |
| L1000H1020 | 0.23 |
| L1000H1035 | 0.22 |
| L1000H1008 | 0.21 |
| L1000H1025 | 0.21 |
| L1000H1030 | 0.20 |
| L1000H1012 | 0.18 |
| L1000H1022 | 0.18 |
| L1022H1000 | 0.16 |
| L1012H1031 | 0.16 |
| L1000H1017 | 0.13 |
| L1000H1010 | 0.11 |
| L1000H1026 | 0.11 |
| L1012H1020 | 0.11 |
| L1012H1029 | 0.11 |
| L1000H1036 | 0.10 |
| L1000H1018 | 0.09 |
| L1000H1034 | 0.09 |
| L1000H1011 | 0.09 |
| L1000H1033 | 0.08 |
| L1012H1016 | 0.08 |
| L1018H1000 | 0.06 |
| L1023H1000 | 0.05 |
| L1000H1038 | 0.04 |
| L1000H1019 | 0.02 |
| L1012H1027 | 0.02 |
| L1014H1000 | 0.01 |
| L1000H1037 | −0.01 |

Example 4: Pharmacokinetics of the Antibodies of
the Present Invention in Mouse a Series of
Pharmacokinetic Experiments were Carried Out in
Mice to Further Screen Antibodies 6-8 week-old SPF Balb/c mice were selected and injected subcutaneously with antibodies (the antibodies of the present invention or control antibody 2) in a dose of 5 mg/kg (weight of the mouse). Blood samples were collected at the time points before administration (0 h) and at 2, 8, 24, 48, 72, 120, 168, 216, 264, 336 h after administration. For blood sampling, the animals were anesthetized by inhaling isoflurane, and blood samples were taken from the orbital venous plexus, and the sampling volume for each animal was about 0.1 ml; 336 h after administration, the animals were anesthetized by inhaling isoflurane and then euthanized after taking blood in the inferior vena cava.

No anticoagulant was added to the blood samples, and serum was isolated from each sample by centrifugation at 1500 g for 10 min at room temperature within 2 h after blood sampling. The collected supernatants were immediately transferred to new labeled centrifuge tubes and then stored at −70° C. for temporary storage. The concentrations of the antibodies in the mice were determined by ELISA:

1. Preparation of Reagents sIL-4Rα (PEPRO TECH, Catalog Number: 200-04R) solution: sIL-4Rα was taken and 1 ml ddH2O was added therein, mixed up and down, and then a solution of 100 µg/ml was obtained. The solution was stored in a refrigerator at −20° C. after being subpacked.

Sample to be tested: 1 µl of serum collected at different time points was added to 999 µl of PBS containing 1% BSA to prepare a serum sample to be tested of 1:1000 dilution.

Standard sample: The antibody to be tested was diluted to 0.1 µg/ml with PBS containing 1% BSA and 0.1% normal animal serum (Beyotime, Catalog Number: ST023). Afterwards, 200, 400, 600, 800, 900, 950, 990 and 1000 µl of PBS containing 1% BSA and 0.1% normal animal serum were respectively added to 800, 600, 400, 200, 100, 50, 10 and 0 µl of 0.1 µg/ml antibodies to be tested, and thus standard samples of the antibodies of the present invention were prepared with a final concentration of 80, 60, 40, 20, 10, 5, 1, or 0 ng/ml respectively.

2. Detection by ELISA

250 µl of 100 µg/ml sIL-4Rα solution was added to 9.75 ml of PBS, mixed up and down, and then an antigen coating buffer of 2.5 µg/ml was obtained. The prepared antigen coating buffer was added to a 96-well ELISA plate (Corning) with a volume of 100 µl per well. The 96-well ELISA plate was incubated overnight in a refrigerator at 4° C. after being wrapped with preservative film (or covered). On the next day, the 96-well ELISA plate was taken out and the solution therein was discarded, and PBS containing 2% BSA was added thereto with a volume of 300 µl per well. The 96-well ELISA plate was incubated for 2 hours in a refrigerator at 4° C. after being wrapped with preservative film (or covered). Then the 96-well ELISA plate was taken out and the solution therein was discarded, and the plate was washed 3 times with PBST. The diluted standard antibodies and the sera to be detected were sequentially added to the corresponding wells, and three duplicate wells were made for each sample with a volume of 100 µl per well. The ELISA plate was wrapped with preservative film (or covered) and incubated for 1 h at room temperature. Subsequently, the solution in the 96-well ELISA plate was discarded and then the plate was washed with PBST for 3 times. Later, TMB solution (Solarbio, Catalog Number: PR1200) was added to the 96-well ELISA plate row by row with a volume of 100 µl per well. The 96-well ELISA plate was placed at room temperature for 5 minutes, and 2 M H2SO4 solution was added in immediately to terminate the reaction. The 96-well ELISA plate was then placed in flexstation 3 (Molecular Devices), the values of OD450 were read, the data were collected and the results were calculated with Winnonlin software. The pharmacokinetic results were shown in FIG. 1 and Table 6 below.

TABLE 6

Pharmacokinetic results of the antibodies of the present invention in mouse

| Number | | Half life h | Time to peak h | Peak concentration μg/ml | Area Under the drug-time Curve h*μg/ml | Volume of distribution ml/kg | Clearance rate ml/h/kg |
|---|---|---|---|---|---|---|---|
| L1020H1031 | Mean value | 269.34 | 72 | 33.79 | 7679.28 | 138.92 | 0.38 |
| | Standard deviation | 105.73 | 0.00 | 0.42 | 163.91 | 22.48 | 0.09 |
| L1012H1031 | Mean value | 167.27 | 48 | 45.5 | 9852.3 | 91.3 | 0.38 |
| | Standard deviation | 8.52 | 0.00 | 1.86 | 448.34 | 5.58 | 0.00 |
| Control antibody 2 | Mean value | 56.67 | 36 | 7.88 | 1132.68 | 288.92 | 3.79 |
| | Standard deviation | 25.84 | 16.97 | 0.25 | 94.42 | 49.45 | 1.12 |

Example 5: Pharmacokinetics of the Antibodies of the Present Invention in *Macaca Fascicularis*

Figure 2:
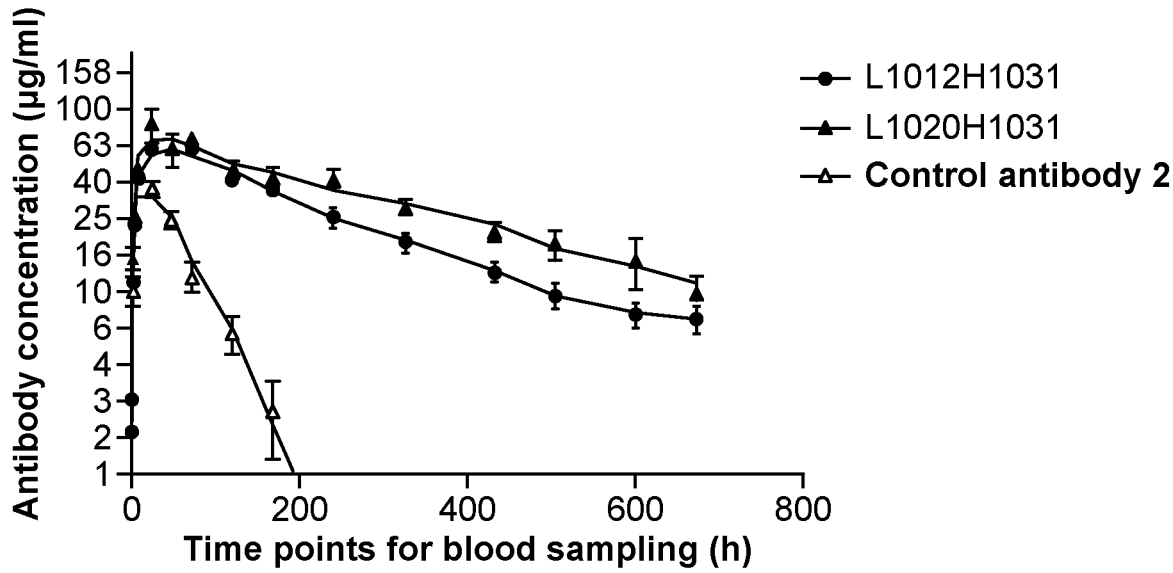
FIG. 2 shows the pharmacokinetic curves of the antibodies of the present invention in *Macaca Fascicularis*.

A series of pharmacokinetic experiments were carried out in *macaca* fascicularises to further screen antibodies.

at −70° C. for temporary storage. The concentrations of the antibodies in the *Macaca Fascicularises* were determined according the method as described in Example 4. The pharmacokinetic results are shown in FIG. 2 and Table 7 below.

TABLE 7

Pharmacokinetic results of the antibodies of the present invention in macaca fascicularis

| Number | | Half life h | Time to peak h | Peak concentration μg/ml | Area Under the drug-time Curve h*μg/ml | Volume of distribution ml/kg | Clearance rate ml/h/kg |
|---|---|---|---|---|---|---|---|
| L1020H1031 | Mean value | 254.95 | 48.00 | 89.65 | 22189.91 | 75.94 | 0.22 |
| | Standard deviation | 44.57 | 33.94 | 44.29 | 8557.15 | 22.95 | 0.10 |
| L1012H1031 | Mean value | 185.75 | 48 | 65 | 16185.73 | 73.41 | 0.28 |
| | Standard deviation | 42.54 | 33.94 | 4.5 | 2506.98 | 0.81 | 0.06 |
| Control antibody 2 | Mean value | 37.03 | 16 | 37.82 | 2773.21 | 93.97 | 1.78 |
| | Standard deviation | 18.03 | 11.31 | 6.75 | 155.84 | 42.47 | 0.07 |

3-5 year-old *macaca* fascicularises each weighting 2-5 Kg were selected and injected subcutaneously with antibodies (the antibodies of the present invention or control antibody 2) in a dose of 5 mg/kg (weight of the *Macaca Fascicularis*). The antibody or control antibody 2 to be administered was accurately extracted with a disposable aseptic injector, and multi-point injections were made subcutaneously on the inner side of the thigh of the animal, and the injection volume per point was not more than 2 ml. Whole blood samples were collected from the subcutaneous vein of the hind limb of the animal at the time points before administration (0 h) and at 0.5, 2, 4, 8, 24, 48, 72, 120, 168, 240, 336 h, 432 h, 504 h, 600 h, 672 h after administration. The blood volume collected from each animal was about 0.1 ml each time.

No anticoagulant was added to the blood samples, and serum was isolated from each sample by centrifugation at 1500 g for 10 min at room temperature within 2 h after blood sampling. The collected supernatants were immediately transferred to new labeled centrifuge tubes and then stored

Example 6: Detection of Binding of the Antibodies of the Present Invention to TF-1 Cells by FACS 1. Cell Culture TF-1 cells (ATCC: CRL-2003™) frozen in liquid nitrogen were taken out, shaken in a 37° C. water bath gently to dissolve quickly. The dissolved cell suspension was transferred to a 15 ml centrifuge tube, and then 1640 medium (Hyclone, Catalog Number: SH30809.01B) was added therein to 10 ml. The tube was centrifuged at 800 rpm for 5 min, the supernatant therein was aspirated off, and the cell pellets were retained and washed once again. The cell density was adjusted to $1 \times 10^5$-$1 \times 10^6$ cells/mi with 1640 medium containing 10% FBS (Hyclone, Catalog Number: SV30184.02) and 2 ng/ml GM-CSF (Sino Biological, Catalog Number: 10015-H01H). The suspension was transferred to a T75 cell culture flask (Nunc), and the cells were statically cultured in an incubator (Thermo) at 37° C., 5% $CO_2$. Every 2-3 days, the cell suspension was taken out, centrifuged at 800 rpm for 5 min, and the cells were resuspended in 10 ml of medium. Subsequently, $1\times10^6$ cells were counted and transferred into a new T75 cell culture flask, and the medium was supplemented thereto to 10 ml. The cells were continuously passaged for 2-3 times to reach a good state (the cells were bright, and had a slightly irregular shape when suspended individually) for experiment.

2. Cell Treatment

Tf-1 cells were taken and counted under a microscope. The cells were divided into three groups and placed into three 1.5 ml centrifuge tubes respectively. The number of cells for each group was $1\times10^6$. The cells were centrifuged at 800 rpm for 5 min, and then resuspended in 1 ml of cold PBS containing 1% BSA for washing once again. Subsequently, the cells were centrifuged at 800 rpm for 5 min, and 45 µl of cold PBS containing 1% BSA was added to each centrifuge tube to resuspend the cells, and then 5 µl (500 µg/ml) of the present antibody L1021H1031, L1020H1031 or L1012H1031 was added to the first centrifuge tube, and 5 µl of PBS was added to the second centrifuge tube as a negative control. The cells were allowed to stand on ice for 45 min and then centrifuged at 800 rpm for 5 min. Afterwards, the cells were resuspended in 1 ml of cold PBS containing 1% BSA for washing once again, and centrifuged at 800 rpm for 5 min. 499 µl of cold PBS containing 1% BSA was added to each centrifuge tube to resuspend the cells, and then 1 µl of FITC-labeled goat anti-human IgG (H+L) (Beyotime, Catalog Number: A0556) was added thereto. After standing on ice for 45 min, the cells were centrifuged at 800 rpm for 5 min, and resuspended in 1 ml of cold PBS containing 1% BSA for washing once again. Thus, the cells to be detected were obtained.

3. Detection by FACS

Figure 3A:
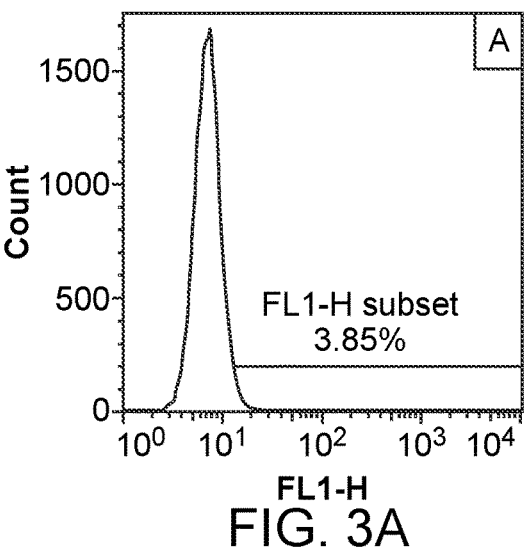
FIGS. 3A-3C show the specific binding of the antibodies of the present invention with TF-1 cells expressing IL-4Rα, as determined by FACS, in which panel 3A shows the fluorescence signal without the addition of antibody L1012H1031 of the present invention; panel 3B shows the fluorescence signal with the addition of antibody L1012H1031 of the present invention; and panel 3C shows the signal superposition of panels 3A and 3B for comparison.
Figure 3B:
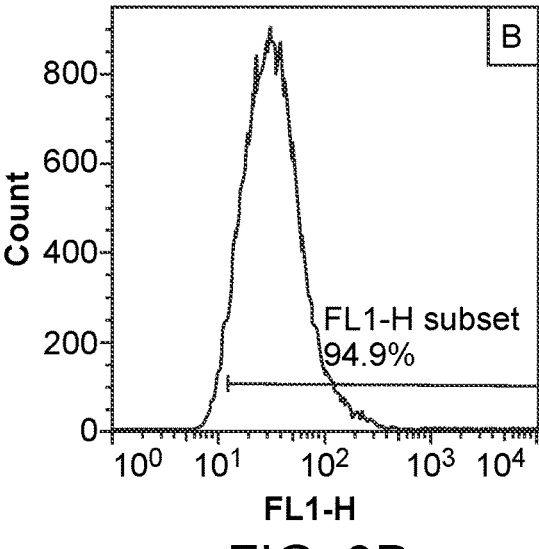
Figure 3C:
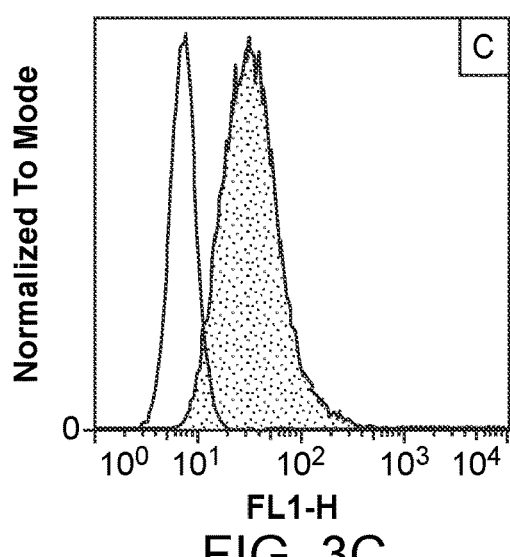
Figure 4A:
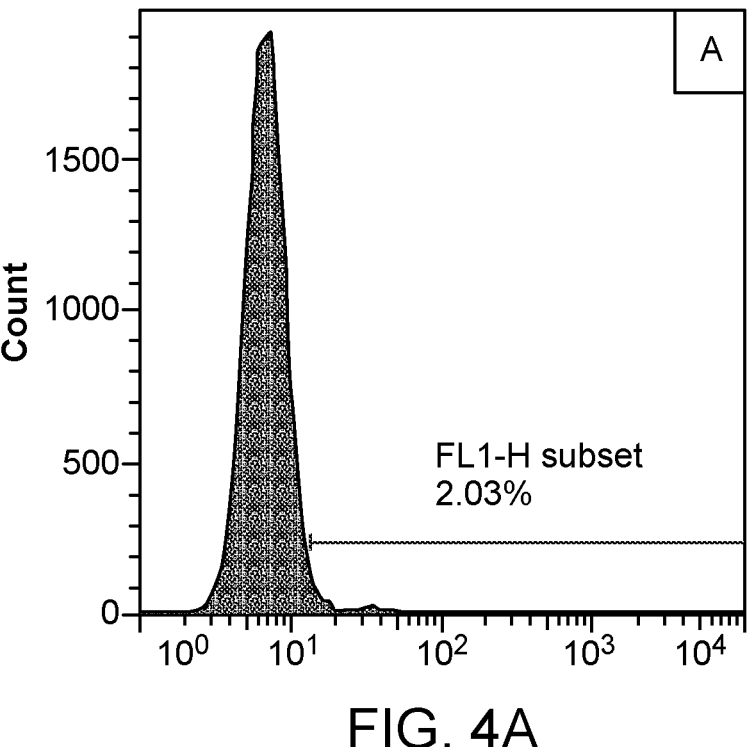
FIGS. 4A-4D show that the specific binding of the antibodies of the present invention with TF-1 cells expressing IL-4Rα is blocked by sIL-4Rα present in the system, as determined by FACS, in which panel 4A shows the fluorescence signal without the addition of antibody L1012H1031 of the present invention; panel 4B shows the fluorescence signal with the addition of antibody L1012H1031 of the present invention; panel 4C shows the fluorescence signal with the addition of antibody L1012H1031 of the present invention and sIL-4Rα; and panel 4D shows the signal superposition of panels 4A-4C for comparison.
Figure 4B:
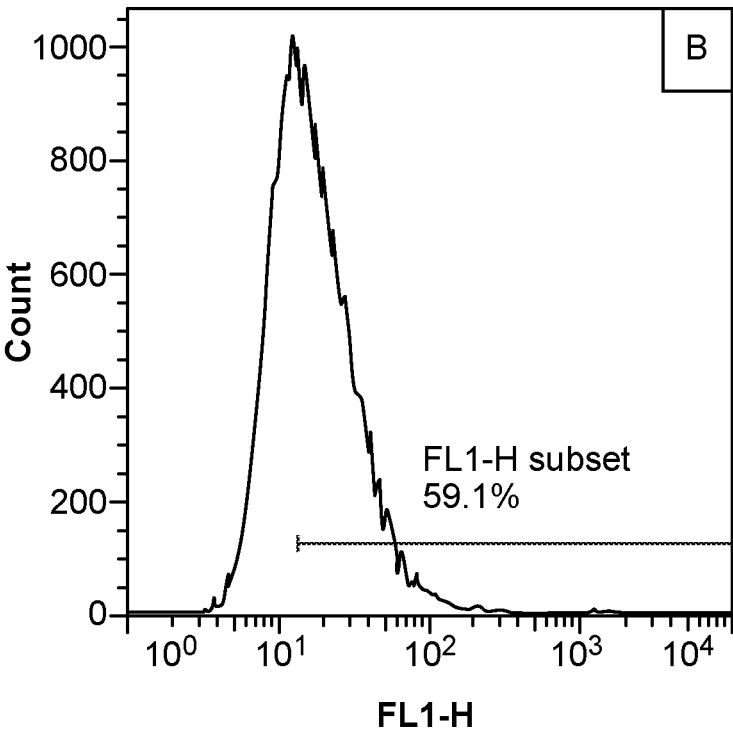
Figure 4C:
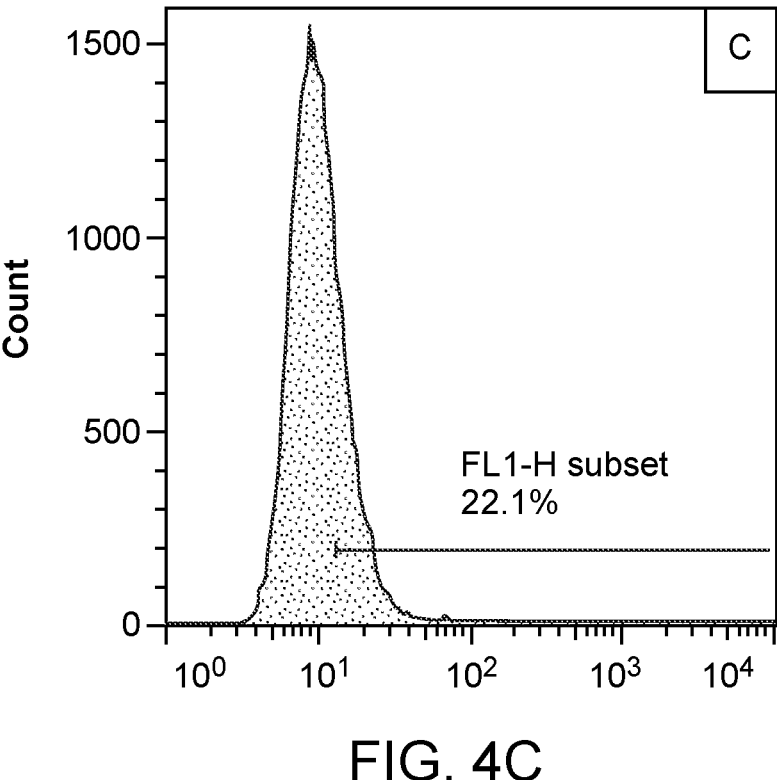
Figure 4D:
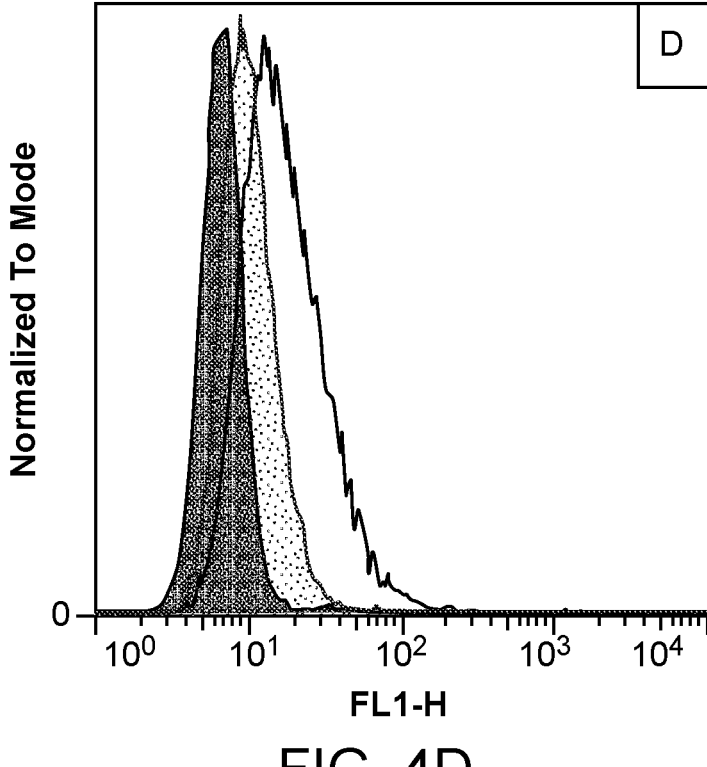

FACS instrument and its operating system were run according to correct protocol. After correct parameters were set, the cells were added into the detection tube to detect fluorescence signal of FL1 channel. The results were analyzed with FlowJo 7.6 software and are shown in FIG. 3, panels 3A-3C. It can be seen that the antibodies of the present invention are capable of specifically binding to TF-1 cells expressing IL-4Rα.

Example 7: Detection of the Blocking Effect of Soluble hIL-4 Rα (sIL-4Rα) on Binding of Antibodies to TF-1 Cells by FACS 1. Preparation of Reagents The hIL-4 (Invivogen, Catalog Number: rhiI-4) solution was prepared as described in Example 2.

2. Cell Culture

The TF-1 cells (ATCC: CRL-2003™) were cultured as described in Example 6.

3. Mixing of sIL-4Rα with the Antibodies of the Present Invention

10 µl (100 µg/ml) of sIL-4Rα and 5 µl (500 µg/ml) of antibody L1021H1031, L1020H1031 or L1012H1031 of the present invention were uniformly mixed in a 1.5 ml centrifuge tube at a molar ratio of 2:1. The mixture of 10 µl PBS and 5 µl of antibody L1021H1031, L1020H1031 or L1012H1031 of the present invention was served as a positive control and 15 µl PBS was served as a negative control. The centrifuge tubes were placed in a 37° C. incubator for 1 h.

4. Cell Treatment

TF-1 cells were taken and then counted under a microscope. The cells were divided into four groups and placed into four 1.5 ml centrifuge tubes respectively. The number of cells for each group was $1\times10^6$. The cells were centrifuged at 800 rpm for 5 min, and then resuspended in 1 ml of cold PBS containing 1% BSA for washing once again. Subsequently, the cells were centrifuged at 800 rpm for 5 min, and 35 µl of cold PBS containing 1% BSA was added to each centrifuge tube to resuspend the cells, and then 15 µl of each of different antibody mixtures and the control prepared in step 3 was added to the tubes respectively. After standing on ice for 45 min, the cells were centrifuged at 800 rpm for 5 min, and resuspended in 1 ml of cold PBS containing 1% BSA for washing once again, and centrifuged at 800 rpm for 5 min. 499 µl of cold PBS containing 1% BSA was added to each centrifuge tube to resuspend the cells, and then 1 µl of FITC-labeled goat anti-human IgG (H+L) (Beyotime, Catalog Number: A0556) was added thereto. After standing on ice for 45 min, the cells were centrifuged at 800 rpm for 5 min, and resuspended in 1 ml of cold PBS containing 1% BSA for washing once again. Thus, the cells to be detected were obtained.

5. Detection by FACS

FACS instrument and its operating system were run according to correct protocol. After correct parameters were set, the cells were added into the detection tube to detect fluorescence signal of FL1 channel. The results were analyzed with FlowJo 7.6 software and are shown in FIG. 4, panels 4A-4D. It can be seen that sIL-4Rα can specifically and effectively block the specific binding of the antibodies of the present invention to TF-1 cells.

Example 8: Determination of Antibody Affinity by Bicore

An anti-human Fc (AHC) antibody (GE Healthcare) was coupled to a CM5 chip, and then the antibody of the present invention was captured by AHC respectively. Subsequently, different concentrations of human sIL-4Rα were flowed through the surface of the chip on which the antibody of the present invention was captured. For capture and binding, the present antibody was diluted to 2 µg/ml and the antigen sIL-4Rα was diluted to 0.39, 0.78, 1.56, 3.13, 6.25, 12.5, 25.0, 50.0 and 100.0 nM. The experimental method was then established in the Biacore T200 control software, after which the experimental program was run for detection. The results are shown in Table 8 below.

TABLE 8

| | Detection results of the antibody affinity | | |
|---|---|---|---|
| Number | Ka ($\times10^5$ M$^{-1}$s$^{-1}$) | Kd ($\times10^{-5}$ s$^{-1}$) | KD ($10^{-10}$ M) |
| Control antibody 1 | 7.63 | 52.3 | 6.85 |
| Control antibody 2 | 3.85 | 1.73 | 0.448 |
| L1020H1031 | 4.61 | 4.79 | 1.04 |
| L1012H1031 | 5.18 | 9.49 | 1.83 |

Example 9: Investigation of the Inhibitory Effect of the Antibodies of the Present Invention on TARC and MDC Release by ELISA 10 ml of fresh blood (donated) anticoagulated with heparin was mixed with PBS at room temperature in a ratio of 1:1, and then the mixture was carefully added to 20 ml of human lymphocyte separation solution (Solarbio, Catalog Number: P8610) prepared in advance. After centrifuging at 1500 rpm for 30 min at room temperature, the PBMC layer was carefully aspirated and washed twice with PBS. The cells were finally diluted with 1640 medium containing 10% FBS and 200 IU/ml IL-2, and then added to a 24-well plate with $1 \times 10^6$ cells per well. Afterwards, antibody L1020H1031 with a final concentration of 1000, 300, 100, 30 or 10 ng/ml was added to each well, following by the addition of IL-4 with a final concentration of 10 ng/ml (or IL-13 with a final concentration of 100 ng/ml) thereto. Detection was carried out according to the method provided with Human TARC ELISA kit (Abcam, Catalog Number: ab183366) or Human MDC ELISA kit (Abcam, Catalog Number: ab179885) after 72 hours of culture.

Figure 5A:
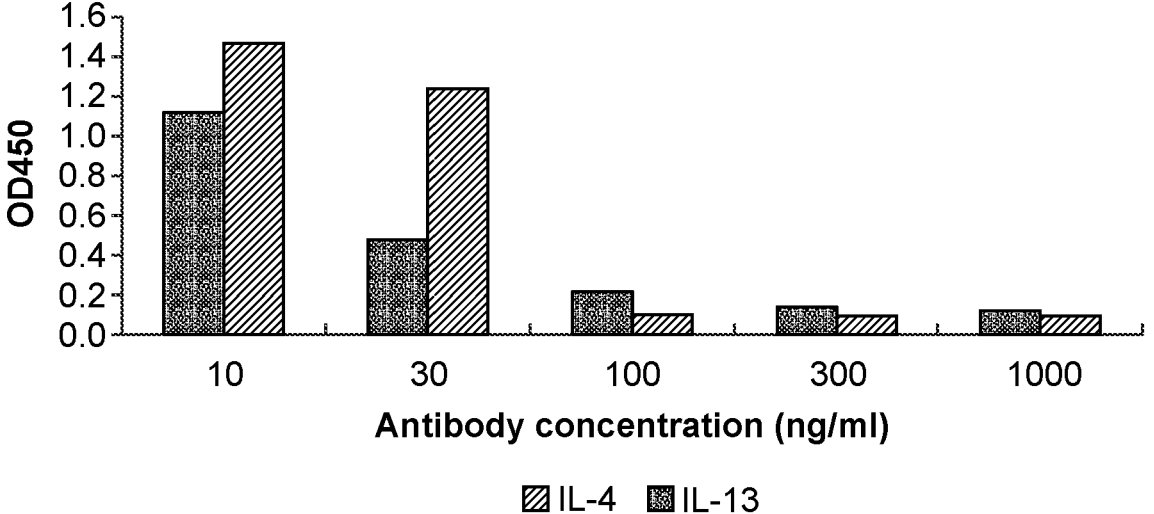
FIGS. 5A-5B show the effect of the antibodies of the present invention on the inhibition of TARC and MDC release, as determined by ELISA, in which panel 5A shows the result that antibody L1020H1031 of the present invention inhibits TARC release, and panel 5B shows the result that antibody L1020H1031 of the present invention inhibits MDC release.
Figure 5B:
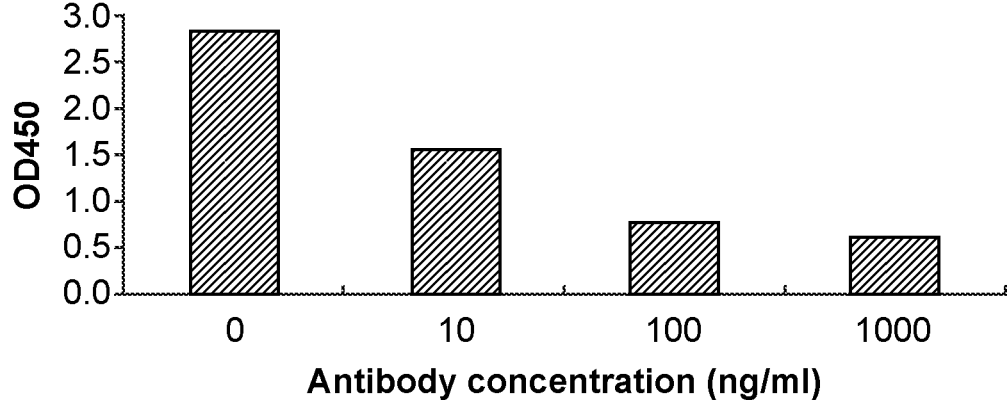

The results are shown in FIG. 5, panels 5A-5B, showing that the antibodies of the present invention can effectively inhibit TARC and MDC release, and the inhibitory effect on release increases with the increasing of antibody concentration.

Example 10: Effect of Specific Amino Acids on the Pharmacokinetics and Expression Levels of the Antibodies of the Invention In vivo pharmacokinetics of the antibodies of the invention are further detected and compared in this Example, in order to investigate the possible effects of specific amino acids at specific positions on the pharmacokinetics of the antibodies in animals. The specific experimental method was the same as that described in Example 4, and the results are shown in Table 9 below.

specific positions on the expression of the antibodies. Culture and transfection of Expi293 cells were conducted according to Example 1, and the collected culture supernatant was then passed through a 0.22 μm filter and then purified by GE MabSelect Sure (Catalog Number: 11003494) Protein A affinity chromatography column in the purification system GE AKTA purifier 10. The purified antibody was collected and concentrated using Amicon ultrafiltration concentrating tube (Catalog Number: UFC903096) and then quantified. The quantitative results are shown in Table 10 below.

TABLE 10

| Detection results of the expression levels of the antibodies of the present invention | |
| --- | --- |
| Antibody | Expression level ($\times 10^{-2}$ mg/ml culture medium) |
| L1020H1031 | 8.39 |
| L1001H1031 | 1.79 |
| L1020H1001 | 4.04 |
| L1012H1001 | 5.00 |
| L1023H1001 | 4.63 |
| L1001H1001 | 1.75 |

From the specific sequence, the amino acid at position 31 in the sequence of the light chain L1012 (SEQ ID NO. 44), L1020 (SEQ ID NO. 55) or L1023 (SEQ ID NO. 51) of the antibody (in CDR1) is Ser (31Ser). Compared with antibod-

TABLE 9

| Detection results of in vivo pharmacokinetics of the antibodies of the present invention | | | | | | | |
| --- | --- | --- | --- | --- | --- | --- | --- |
| | | Half life h | Time to peak h | Peak concentration ug/ml | Area Under the drug-time Curve h*ug/ml | Volume of distribution ml/kg | Clearance rate ml/h/kg |
| L1020H1031 | Mean value | 185.49 | 40 | 38.94 | 8188.8 | 114.28 | 0.43 |
| | Standard deviation | 18.52 | 13.86 | 2.33 | 510.47 | 6.5 | 0.05 |
| L1012H1001 | Mean value | 161.26 | 48.00 | 12.36 | 2491.19 | 332.79 | 1.47 |
| | Standard deviation | 54.30 | 0.00 | 2.26 | 165.16 | 76.91 | 0.20 |
| L1001H1031 | Mean value | 171.41 | 56.00 | 42.74 | 9273.73 | 99.17 | 0.40 |
| | Standard deviation | 6.12 | 13.86 | 7.38 | 1868.66 | 18.69 | 0.07 |
| L1020H1001 | Mean value | 89.00 | 64.00 | 20.11 | 3481.40 | 164.14 | 1.30 |
| | Standard deviation | 16.70 | 13.86 | 2.14 | 268.39 | 22.86 | 0.20 |

From the specific sequence, the amino acid at position 103 in the sequence of the heavy chain H1031 (SEQ ID NO. 91) of the antibody (in CDR3) is Asp (103Asp), and the amino acid at position 104 is Tyr (104Tyr). Compared with antibodies that have no 103Asp and 104Tyr in heavy chain, the present antibodies which have 103Asp and 104Tyr have a 2- to 4-fold higher area under the drug-time curve and an about 70% reduced clearance rate.

The expression levels of the antibodies of the present invention are also detected and compared, in order to investigate the possible effects of specific amino acids at ies that have no 31Ser in light chain, the present antibodies which have 31Ser have a 2- to 5-fold higher expression level.

The above description for the embodiments of the present invention is not intended to limit the present invention, and those skilled in the art can make various changes and variations according to the present invention, which are within the protection scope of the claims of the present invention without departing from the spirit of the same.

45

The invention claimed is:

1. An isolated nucleic acid or set of nucleic acids encoding an isolated anti-interleukin 4 receptor (IL-4R) antibody comprising a heavy chain variable domain (VH) comprising three heavy chain complementarity determining regions (CDRs) (CDR-H1, CDR-H2, and CDR-H3), and a light chain variable domain (VL) comprising three light chain CDRs (CDR-L1, CDR-L2, and CDR-L3) wherein:

a. the CDR-L1 comprises the amino acid sequence set forth in SEQ ID NO: 2, the CDR-L2 comprises the amino acid sequence set forth in SEQ ID NO: 3, the CDR-L3 comprises the amino acid sequence set forth in SEQ ID NO: 8, the CDR-H1 comprises the amino acid sequence set forth in SEQ ID NO: 14, the CDR-H2 comprises the amino acid sequence set forth in SEQ ID NO: 18, and the CDR-H3 comprises the amino acid sequence set forth in SEQ ID NO: 19;

b. the CDR-L1 comprises the amino acid sequence set forth in SEQ ID NO: 2, the CDR-L2 comprises the amino acid sequence set forth in SEQ ID NO: 4, the CDR-L3 comprises the amino acid sequence set forth in SEQ ID NO: 8, the CDR-H1 comprises the amino acid sequence set forth in SEQ ID NO: 14, the CDR-H2 comprises the amino acid sequence set forth in SEQ ID NO: 18, and the CDR-H3 comprises the amino acid sequence set forth in SEQ ID NO: 19; or c. the CDR-L1 comprises the amino acid sequence set forth in SEQ ID NO: 2, the CDR-L2 comprises the amino acid sequence set forth in SEQ ID NO: 4, the CDR-L3 comprises the amino acid sequence set forth in SEQ ID NO: 5, the CDR-H1 comprises the amino acid sequence set forth in SEQ ID NO: 14, the CDR-H2 comprises the amino acid sequence set forth in SEQ ID NO: 18, and the CDR-H3 comprises the amino acid sequence set forth in SEQ ID NO: 19.

2. The isolated nucleic acid or set of nucleic acids of claim 1, wherein the CDR-L1 comprises the amino acid sequence set forth in SEQ ID NO: 2, the CDR-L2 comprises the amino acid sequence set forth in SEQ ID NO: 3, the CDR-L3 comprises the amino acid sequence set forth in SEQ ID NO: 8, the CDR-H1 comprises the amino acid sequence set forth in SEQ ID NO: 14, the CDR-H2 comprises the amino acid sequence set forth in SEQ ID NO: 18, and the CDR-H3 comprises the amino acid sequence set forth in SEQ ID NO: 19.

3. The isolated nucleic acid or set of nucleic acids of claim 1, wherein the CDR-L1 comprises the amino acid sequence set forth in SEQ ID NO: 2, the CDR-L2 comprises the amino acid sequence set forth in SEQ ID NO: 4, the CDR-L3 comprises the amino acid sequence set forth in SEQ ID NO: 8, the CDR-H1 comprises the amino acid sequence set forth in SEQ ID NO: 14, the CDR-H2 comprises the amino acid sequence set forth in SEQ ID NO: 18, and the CDR-H3 comprises the amino acid sequence set forth in SEQ ID NO: 19.

4. The isolated nucleic acid or set of nucleic acids of claim 1, wherein the CDR-L1 comprises the amino acid sequence set forth in SEQ ID NO: 2, the CDR-L2 comprises the amino acid sequence set forth in SEQ ID NO: 4, the CDR-L3 comprises the amino acid sequence set forth in SEQ ID NO: 5, the CDR-H1 comprises the amino acid sequence set forth in SEQ ID NO: 14, the CDR-H2 comprises the amino acid sequence set forth in SEQ ID NO: 18, and the CDR-H3 comprises the amino acid sequence set forth in SEQ ID NO: 19.

5. The isolated nucleic acid or set of nucleic acids of claim 1, wherein:

a. the VL comprises the amino acid sequence set forth in SEQ ID NO: 55 and the VH comprises the amino acid sequence set forth in SEQ ID NO: 91;

b. the VL comprises the amino acid sequence set forth in SEQ ID NO: 54 and the VH comprises the amino acid sequence set forth in SEQ ID NO: 91; or c. the VL comprises the amino acid sequence set forth in SEQ ID NO: 44 and the VH comprises the amino acid sequence set forth in SEQ ID NO: 91.

6. A vector comprising the isolated nucleic acid or set of nucleic acids of claim 5.

7. A host comprising the isolated nucleic acid or set of nucleic acids of claim 5.

8. A method of producing an isolated anti-IL-4R antibody, comprising expressing the isolated antibody with the host cell of claim 7 and isolating the expressed antibody.

9. The isolated nucleic acid or set of nucleic acids of claim 1, wherein the VL comprises the amino acid sequence set forth in SEQ ID NO: 55 and the VH comprises the amino acid sequence set forth in SEQ ID NO: 91.

10. The isolated nucleic acid or set of nucleic acids of claim 9, wherein the isolated antibody is a human IgG4 subtype.

11. A vector comprising the isolated nucleic acid or set of nucleic acids of claim 10.

12. A host comprising the isolated nucleic acid or set of nucleic acids of claim 10.

13. A method of producing an isolated anti-IL-4R antibody, comprising expressing the isolated antibody with the host cell of claim 12 and isolating the expressed antibody.

14. A vector comprising the isolated nucleic acid or set of nucleic acids of claim 9.

15. A host comprising the isolated nucleic acid or set of nucleic acids of claim 9.

16. A method of producing an isolated anti-IL-4R antibody, comprising expressing the isolated antibody with the host cell of claim 15 and isolating the expressed antibody.

17. The isolated nucleic acid or set of nucleic acids of claim 1, wherein the VL comprises the amino acid sequence set forth in SEQ ID NO: 54 and the VH comprises the amino acid sequence set forth in SEQ ID NO: 91.

18. The isolated nucleic acid or set of nucleic acids of claim 1, wherein the VL comprises the amino acid sequence set forth in SEQ ID NO: 44 and the VH comprises the amino acid sequence set forth in SEQ ID NO: 91.

19. The isolated nucleic acid or set of nucleic acids of claim 1, wherein the isolated antibody binds to human IL-4Rα.

20. The isolated nucleic acid or set of nucleic acids of claim 1, wherein the isolated antibody binds to soluble human IL-4Rα.

21. The isolated nucleic acid or set of nucleic acids of claim 1, wherein the isolated antibody is a monoclonal antibody.

22. The isolated nucleic acid or set of nucleic acids of claim 1, wherein the isolated antibody is an immunoglobulin having a human isotype of IgA, IgD, IgE, IgG or IgM.

23. The isolated nucleic acid or set of nucleic acids of claim 1, wherein the isolated antibody is a human IgG1, IgG2, IgG3, or IgG4 subtype.

24. The isolated nucleic acid or set of nucleic acids of claim 1, wherein the isolated antibody is a human IgG4 subtype.

25. A vector comprising the isolated nucleic acid or set of nucleic acids of claim 24.

26. A host comprising the isolated nucleic acid or set of nucleic acids of claim 24.

27. A method of producing an isolated anti-IL-4R antibody, comprising expressing the isolated antibody with the host cell of claim 26 and isolating the expressed antibody.

28. A vector comprising the isolated nucleic acid or set of nucleic acids of claim 1.

29. A host comprising the isolated nucleic acid or set of nucleic acids of claim 1.

30. A method of producing an isolated antibody which binds to IL-4R, comprising expressing the isolated antibody with the host cell of claim 29 and isolating the expressed antibody.

* * * * *

SEQUENCE LISTING

Sequence total quantity: 94

SEQ ID NO: 1          moltype = AA  length = 12
FEATURE               Location/Qualifiers
REGION                1..12
                      note = LCDR1-1
source                1..12
                      mol_type = protein
                      organism = synthetic construct
SEQUENCE: 1
RASQSVSNSY LA                                                    12

SEQ ID NO: 2          moltype = AA  length = 12
FEATURE               Location/Qualifiers
REGION                1..12
                      note = LCDR1-2
source                1..12
                      mol_type = protein
                      organism = synthetic construct
SEQUENCE: 2
RASQSVSSSY LA                                                    12

SEQ ID NO: 3          moltype = AA  length = 7
FEATURE               Location/Qualifiers
REGION                1..7
                      note = LCDR2-1
source                1..7
                      mol_type = protein
                      organism = synthetic construct
SEQUENCE: 3
GASSRAT                                                          7

SEQ ID NO: 4          moltype = AA  length = 7
FEATURE               Location/Qualifiers
REGION                1..7
                      note = LCDR2-2
source                1..7
                      mol_type = protein
                      organism = synthetic construct
SEQUENCE: 4
GASSRAP                                                          7

SEQ ID NO: 5          moltype = AA  length = 10
FEATURE               Location/Qualifiers
REGION                1..10
                      note = LCDR3-1
source                1..10
                      mol_type = protein
                      organism = synthetic construct
SEQUENCE: 5
QQYGSSPPWT                                                       10

SEQ ID NO: 6          moltype = AA  length = 10
FEATURE               Location/Qualifiers
REGION                1..10
                      note = LCDR3-2
source                1..10
                      mol_type = protein
                      organism = synthetic construct
SEQUENCE: 6
QQYDHSPPWT                                                       10

SEQ ID NO: 7          moltype = AA  length = 10
FEATURE               Location/Qualifiers
REGION                1..10
                      note = LCDR3-3
source                1..10
                      mol_type = protein
                      organism = synthetic construct
SEQUENCE: 7
QQYGSSAGWT                                                       10

SEQ ID NO: 8          moltype = AA  length = 10
FEATURE               Location/Qualifiers
REGION                1..10
                      note = LCDR3-4
source                1..10
                      mol_type = protein
                      organism = synthetic construct -continued

```
SEQUENCE: 8
QQYDHSAGWT                                                          10

SEQ ID NO: 9          moltype = AA   length = 23
FEATURE               Location/Qualifiers
REGION                1..23
                      note = LFR1-1
source                1..23
                      mol_type = protein
                      organism = synthetic construct
SEQUENCE: 9
EIVLTQSPGT LSLSPGERAT LSC                                           23

SEQ ID NO: 10         moltype = AA   length = 15
FEATURE               Location/Qualifiers
REGION                1..15
                      note = LFR2-1
source                1..15
                      mol_type = protein
                      organism = synthetic construct
SEQUENCE: 10
WYQQKPGQAP RLLIF                                                    15

SEQ ID NO: 11         moltype = AA   length = 15
FEATURE               Location/Qualifiers
REGION                1..15
                      note = LFR2-2
source                1..15
                      mol_type = protein
                      organism = synthetic construct
SEQUENCE: 11
WYQQKPGQAP RLLIY                                                    15

SEQ ID NO: 12         moltype = AA   length = 32
FEATURE               Location/Qualifiers
REGION                1..32
                      note = LFR3-1
source                1..32
                      mol_type = protein
                      organism = synthetic construct
SEQUENCE: 12
GIPDRFSGSG SGTDFTLTIS RLEPEDFAVY YC                                 32

SEQ ID NO: 13         moltype = AA   length = 10
FEATURE               Location/Qualifiers
REGION                1..10
                      note = LFR4-1
source                1..10
                      mol_type = protein
                      organism = synthetic construct
SEQUENCE: 13
FGQGTKVEIK                                                          10

SEQ ID NO: 14         moltype = AA   length = 5
FEATURE               Location/Qualifiers
REGION                1..5
                      note = HCDR1-1
source                1..5
                      mol_type = protein
                      organism = synthetic construct
SEQUENCE: 14
RNAMF                                                                5

SEQ ID NO: 15         moltype = AA   length = 5
FEATURE               Location/Qualifiers
REGION                1..5
                      note = HCDR1-2
source                1..5
                      mol_type = protein
                      organism = synthetic construct
SEQUENCE: 15
RNAMH                                                                5

SEQ ID NO: 16         moltype = AA   length = 5
FEATURE               Location/Qualifiers
REGION                1..5
                      note = HCDR1-3
source                1..5
                      mol_type = protein
```

-continued

```
                              organism = synthetic construct
SEQUENCE: 16
DYAMF                                                            5

SEQ ID NO: 17              moltype = AA   length = 17
FEATURE                    Location/Qualifiers
REGION                     1..17
                           note = HCDR2-1
source                     1..17
                           mol_type = protein
                           organism = synthetic construct
SEQUENCE: 17
GIGTGGATNY ADSVKGR                                              17

SEQ ID NO: 18              moltype = AA   length = 17
FEATURE                    Location/Qualifiers
REGION                     1..17
                           note = HCDR2-2
source                     1..17
                           mol_type = protein
                           organism = synthetic construct
SEQUENCE: 18
GIGTGGATSY ADSVKGR                                              17

SEQ ID NO: 19              moltype = AA   length = 7
FEATURE                    Location/Qualifiers
REGION                     1..7
                           note = HCDR3-1
source                     1..7
                           mol_type = protein
                           organism = synthetic construct
SEQUENCE: 19
GRYYFDY                                                          7

SEQ ID NO: 20              moltype = AA   length = 7
FEATURE                    Location/Qualifiers
REGION                     1..7
                           note = HCDR3-2
source                     1..7
                           mol_type = protein
                           organism = synthetic construct
SEQUENCE: 20
GRYYFPW                                                          7

SEQ ID NO: 21              moltype = AA   length = 30
FEATURE                    Location/Qualifiers
REGION                     1..30
                           note = HFR1-1
source                     1..30
                           mol_type = protein
                           organism = synthetic construct
SEQUENCE: 21
EVQLVESGGG LVHPGGSLRL SCAGSGFTFS                                30

SEQ ID NO: 22              moltype = AA   length = 30
FEATURE                    Location/Qualifiers
REGION                     1..30
                           note = HFR1-2
source                     1..30
                           mol_type = protein
                           organism = synthetic construct
SEQUENCE: 22
EVQLVQSGGG LVQPGGSLRL SCAGSGFTFS                                30

SEQ ID NO: 23              moltype = AA   length = 30
FEATURE                    Location/Qualifiers
REGION                     1..30
                           note = HFR1-3
source                     1..30
                           mol_type = protein
                           organism = synthetic construct
SEQUENCE: 23
EVQLVQSGGG LVHPGGSLRL SCAASGFTFS                                30

SEQ ID NO: 24              moltype = AA   length = 30
FEATURE                    Location/Qualifiers
REGION                     1..30
                           note = HFR1-4
source                     1..30
```

```
                            mol_type = protein
                            organism = synthetic construct
SEQUENCE: 24
EVQLVQSGGG LVHPGGSLRL SCAGSGFTFS                                                   30

SEQ ID NO: 25              moltype = AA  length = 30
FEATURE                    Location/Qualifiers
REGION                     1..30
                           note = HFR1-5
source                     1..30
                           mol_type = protein
                           organism = synthetic construct
SEQUENCE: 25
EVQLVESGGG LVQPGGSLRL SCAGSGFTFS                                                   30

SEQ ID NO: 26              moltype = AA  length = 30
FEATURE                    Location/Qualifiers
REGION                     1..30
                           note = HFR1-6
source                     1..30
                           mol_type = protein
                           organism = synthetic construct
SEQUENCE: 26
EVQLVESGGG LVHPGGSLRL SCAASGFTFS                                                   30

SEQ ID NO: 27              moltype = AA  length = 30
FEATURE                    Location/Qualifiers
REGION                     1..30
                           note = HFR1-7
source                     1..30
                           mol_type = protein
                           organism = synthetic construct
SEQUENCE: 27
EVQLVQSGGG LVQPGGSLRL SCAASGFTFS                                                   30

SEQ ID NO: 28              moltype = AA  length = 30
FEATURE                    Location/Qualifiers
REGION                     1..30
                           note = HFR1-8
source                     1..30
                           mol_type = protein
                           organism = synthetic construct
SEQUENCE: 28
EVQLVESGGG LVQPGGSLRL SCAASGFTFS                                                   30

SEQ ID NO: 29              moltype = AA  length = 30
FEATURE                    Location/Qualifiers
REGION                     1..30
                           note = HFR1-9
source                     1..30
                           mol_type = protein
                           organism = synthetic construct
SEQUENCE: 29
EVQLVQSGGG LVHPGRSLRL SCAGSGFTFS                                                   30

SEQ ID NO: 30              moltype = AA  length = 30
FEATURE                    Location/Qualifiers
REGION                     1..30
                           note = HFR1-10
source                     1..30
                           mol_type = protein
                           organism = synthetic construct
SEQUENCE: 30
EVQLVQSGGG LVHPGGSLRL TCAGSGFTFS                                                   30

SEQ ID NO: 31              moltype = AA  length = 30
FEATURE                    Location/Qualifiers
REGION                     1..30
                           note = HFR1-11
source                     1..30
                           mol_type = protein
                           organism = synthetic construct
SEQUENCE: 31
EVQLVQSGGG LVHPGGSLRL SCAGSGFTFD                                                   30

SEQ ID NO: 32              moltype = AA  length = 14
FEATURE                    Location/Qualifiers
REGION                     1..14
                           note = HFR2-1
```

-continued

```
source                  1..14
                        mol_type = protein
                        organism = synthetic construct
SEQUENCE: 32
WVRQAPGKGL EWVS                                                   14

SEQ ID NO: 33           moltype = AA  length = 14
FEATURE                 Location/Qualifiers
REGION                  1..14
                        note = HFR2-2
source                  1..14
                        mol_type = protein
                        organism = synthetic construct
SEQUENCE: 33
WVRQAPGEGL EWVS                                                   14

SEQ ID NO: 34           moltype = AA  length = 31
FEATURE                 Location/Qualifiers
REGION                  1..31
                        note = HFR3-1
source                  1..31
                        mol_type = protein
                        organism = synthetic construct
SEQUENCE: 34
FTISRDNAKN SLYLQMNSLR AEDMAVYYCA R                                31

SEQ ID NO: 35           moltype = AA  length = 31
FEATURE                 Location/Qualifiers
REGION                  1..31
                        note = HFR3-2
source                  1..31
                        mol_type = protein
                        organism = synthetic construct
SEQUENCE: 35
FTISRDNAKN SLYLQMNSLR AEDTAVYYCA R                                31

SEQ ID NO: 36           moltype = AA  length = 31
FEATURE                 Location/Qualifiers
REGION                  1..31
                        note = HFR3-3
source                  1..31
                        mol_type = protein
                        organism = synthetic construct
SEQUENCE: 36
FTISRDEAKN SLYLQMNSLR AEDMAVYYCA R                                31

SEQ ID NO: 37           moltype = AA  length = 31
FEATURE                 Location/Qualifiers
REGION                  1..31
                        note = HFR3-4
source                  1..31
                        mol_type = protein
                        organism = synthetic construct
SEQUENCE: 37
FTISRDNAKN SLYLQMNSLR AGDMAVYYCA R                                31

SEQ ID NO: 38           moltype = AA  length = 11
FEATURE                 Location/Qualifiers
REGION                  1..11
                        note = HFR4-1
source                  1..11
                        mol_type = protein
                        organism = synthetic construct
SEQUENCE: 38
WGQGTLVTVS S                                                      11

SEQ ID NO: 39           moltype = AA  length = 109
FEATURE                 Location/Qualifiers
REGION                  1..109
                        note = VL L1007
source                  1..109
                        mol_type = protein
                        organism = synthetic construct
SEQUENCE: 39
EIVLTQSPGT LSLSPGERAT LSCRASQSVS NSYLAWYQQK PGQAPRLLIF GASSRATGIP  60
DRFSGSGSGT DFTLTISRLE PEDFAVYYCQ QYGSSPPWTF GQGTKVEIK            109

SEQ ID NO: 40           moltype = AA  length = 109
FEATURE                 Location/Qualifiers
```

```
REGION                    1..109
                          note = VL L1008
source                    1..109
                          mol_type = protein
                          organism = synthetic construct
SEQUENCE: 40
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPPWTF GQGTKVEIK             109

SEQ ID NO: 41             moltype = AA  length = 109
FEATURE                   Location/Qualifiers
REGION                    1..109
                          note = VL L1009
source                    1..109
                          mol_type = protein
                          organism = synthetic construct
SEQUENCE: 41
EIVLTQSPGT LSLSPGERAT LSCRASQSVS SSYLAWYQQK PGQAPRLLIF GASSRAPGIP  60
DRFSGSGSGT DFTLTISRLE PEDFAVYYCQ QYGSSPPWTF GQGTKVEIK             109

SEQ ID NO: 42             moltype = AA  length = 109
FEATURE                   Location/Qualifiers
REGION                    1..109
                          note = VL L1010
source                    1..109
                          mol_type = protein
                          organism = synthetic construct
SEQUENCE: 42
EIVLTQSPGT LSLSPGERAT LSCRASQSVS NSYLAWYQQK PGQAPRLLIY GASSRATGIP  60
DRFSGSGSGT DFTLTISRLE PEDFAVYYCQ QYGSSPPWTF GQGTKVEIK             109

SEQ ID NO: 43             moltype = AA  length = 109
FEATURE                   Location/Qualifiers
REGION                    1..109
                          note = VL L1011
source                    1..109
                          mol_type = protein
                          organism = synthetic construct
SEQUENCE: 43
EIVLTQSPGT LSLSPGERAT LSCRASQSVS NSYLAWYQQK PGQAPRLLIF GASSRAPGIP  60
DRFSGSGSGT DFTLTISRLE PEDFAVYYCQ QYGSSPPWTF GQGTKVEIK             109

SEQ ID NO: 44             moltype = AA  length = 109
FEATURE                   Location/Qualifiers
REGION                    1..109
                          note = VL L1012
source                    1..109
                          mol_type = protein
                          organism = synthetic construct
SEQUENCE: 44
EIVLTQSPGT LSLSPGERAT LSCRASQSVS SSYLAWYQQK PGQAPRLLIY GASSRAPGIP  60
DRFSGSGSGT DFTLTISRLE PEDFAVYYCQ QYGSSPPWTF GQGTKVEIK             109

SEQ ID NO: 45             moltype = AA  length = 109
FEATURE                   Location/Qualifiers
REGION                    1..109
                          note = VL L1016
source                    1..109
                          mol_type = protein
                          organism = synthetic construct
SEQUENCE: 45
EIVLTQSPGT LSLSPGERAT LSCRASQSVS SSYLAWYQQK PGQAPRLLIF GASSRATGIP  60
DRFSGSGSGT DFTLTISRLE PEDFAVYYCQ QYDHSPPWTF GQGTKVEIK             109

SEQ ID NO: 46             moltype = AA  length = 109
FEATURE                   Location/Qualifiers
REGION                    1..109
                          note = VL L1017
source                    1..109
                          mol_type = protein
                          organism = synthetic construct
SEQUENCE: 46
EIVLTQSPGT LSLSPGERAT LSCRASQSVS SSYLAWYQQK PGQAPRLLIF GASSRATGIP  60
DRFSGSGSGT DFTLTISRLE PEDFAVYYCQ QYGSSAGWTF GQGTKVEIK             109

SEQ ID NO: 47             moltype = AA  length = 109
FEATURE                   Location/Qualifiers
REGION                    1..109
                          note = VL L1018
```

-continued

```
source                  1..109
                        mol_type = protein
                        organism = synthetic construct
SEQUENCE: 47
EIVLTQSPGT LSLSPGERAT LSCRASQSVS SSYLAWYQQK PGQAPRLLIF GASSRATGIP  60
DRFSGSGSGT DFTLTISRLE PEDFAVYYCQ QYDHSAGWTF GQGTKVEIK              109

SEQ ID NO: 48           moltype = AA  length = 109
FEATURE                 Location/Qualifiers
REGION                  1..109
                        note = VL L1013
source                  1..109
                        mol_type = protein
                        organism = synthetic construct
SEQUENCE: 48
EIVLTQSPGT LSLSPGERAT LSCRASQSVS NSYLAWYQQK PGQAPRLLIF GASSRATGIP  60
DRFSGSGSGT DFTLTISRLE PEDFAVYYCQ QYDHSPPWTF GQGTKVEIK              109

SEQ ID NO: 49           moltype = AA  length = 109
FEATURE                 Location/Qualifiers
REGION                  1..109
                        note = VL L1014
source                  1..109
                        mol_type = protein
                        organism = synthetic construct
SEQUENCE: 49
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYDHSPPWTF GQGTKVEIK              109

SEQ ID NO: 50           moltype = AA  length = 109
FEATURE                 Location/Qualifiers
REGION                  1..109
                        note = VL L1015
source                  1..109
                        mol_type = protein
                        organism = synthetic construct
SEQUENCE: 50
EIVLTQSPGT LSLSPGERAT LSCRASQSVS SSYLAWYQQK PGQAPRLLIF GASSRAPGIP  60
DRFSGSGSGT DFTLTISRLE PEDFAVYYCQ QYDHSPPWTF GQGTKVEIK              109

SEQ ID NO: 51           moltype = AA  length = 109
FEATURE                 Location/Qualifiers
REGION                  1..109
                        note = VL L1023
source                  1..109
                        mol_type = protein
                        organism = synthetic construct
SEQUENCE: 51
EIVLTQSPGT LSLSPGERAT LSCRASQSVS SSYLAWYQQK PGQAPRLLIY GASSRAPGIP  60
DRFSGSGSGT DFTLTISRLE PEDFAVYYCQ QYDHSAGWTF GQGTKVEIK              109

SEQ ID NO: 52           moltype = AA  length = 109
FEATURE                 Location/Qualifiers
REGION                  1..109
                        note = VL L1024
source                  1..109
                        mol_type = protein
                        organism = synthetic construct
SEQUENCE: 52
EIVLTQSPGT LSLSPGERAT LSCRASQSVS NSYLAWYQQK PGQAPRLLIF GASSRAPGIP  60
DRFSGSGSGT DFTLTISRLE PEDFAVYYCQ QYDHSAGWTF GQGTKVEIK              109

SEQ ID NO: 53           moltype = AA  length = 109
FEATURE                 Location/Qualifiers
REGION                  1..109
                        note = VL L1022
source                  1..109
                        mol_type = protein
                        organism = synthetic construct
SEQUENCE: 53
EIVLTQSPGT LSLSPGERAT LSCRASQSVS NSYLAWYQQK PGQAPRLLIY GASSRATGIP  60
DRFSGSGSGT DFTLTISRLE PEDFAVYYCQ QYDHSAGWTF GQGTKVEIK              109

SEQ ID NO: 54           moltype = AA  length = 109
FEATURE                 Location/Qualifiers
REGION                  1..109
                        note = VL L1021
source                  1..109
                        mol_type = protein
```

```
                              organism = synthetic construct
SEQUENCE: 54
EIVLTQSPGT LSLSPGERAT LSCRASQSVS SSYLAWYQQK PGQAPRLLIF GASSRAPGIP    60
DRFSGSGSGT DFTLTISRLE PEDFAVYYCQ QYDHSAGWTF GQGTKVEIK               109

SEQ ID NO: 55          moltype = AA  length = 109
FEATURE                Location/Qualifiers
REGION                 1..109
                       note = VL L1020
source                 1..109
                       mol_type = protein
                       organism = synthetic construct
SEQUENCE: 55
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QYDHSAGWTF GQGTKVEIK               109

SEQ ID NO: 56          moltype = AA  length = 109
FEATURE                Location/Qualifiers
REGION                 1..109
                       note = VL L1019
source                 1..109
                       mol_type = protein
                       organism = synthetic construct
SEQUENCE: 56
EIVLTQSPGT LSLSPGERAT LSCRASQSVS NSYLAWYQQK PGQAPRLLIF GASSRATGIP    60
DRFSGSGSGT DFTLTISRLE PEDFAVYYCQ QYDHSAGWTF GQGTKVEIK               109

SEQ ID NO: 57          moltype = AA  length = 109
FEATURE                Location/Qualifiers
REGION                 1..109
                       note = VL L1000
source                 1..109
                       mol_type = protein
                       organism = synthetic construct
SEQUENCE: 57
EIVLTQSPGT LSLSPGERAT LSCRASQSVS SSYLAWYQQK PGQAPRLLIF GASSRATGIP    60
DRFSGSGSGT DFTLTISRLE PEDFAVYYCQ QYGSSPPWTF GQGTKVEIK               109

SEQ ID NO: 58          moltype = AA  length = 109
FEATURE                Location/Qualifiers
REGION                 1..109
                       note = VL L1001
source                 1..109
                       mol_type = protein
                       organism = synthetic construct
SEQUENCE: 58
EIVLTQSPGT LSLSPGERAT LSCRASQSVS NSYLAWYQQK PGQAPRLLIY GASSRAPGIP    60
DRFSGSGSGT DFTLTISRLE PEDFAVYYCQ QYDHSAGWTF GQGTKVEIK               109

SEQ ID NO: 59          moltype = AA  length = 115
FEATURE                Location/Qualifiers
REGION                 1..115
                       note = VH H1009
source                 1..115
                       mol_type = protein
                       organism = synthetic construct
SEQUENCE: 59
EVQLVESGGG LVHPGGSLRL SCAGSGFTFS RNAMFWVRQA PGKGLEWVSG IGTGGATNYA    60
DSVKGRFTIS RDNAKNSLYL QMNSLRAEDM AVYYCARGRY YFDYWGQGTL VTVSS        115

SEQ ID NO: 60          moltype = AA  length = 115
FEATURE                Location/Qualifiers
REGION                 1..115
                       note = VH H1010
source                 1..115
                       mol_type = protein
                       organism = synthetic construct
SEQUENCE: 60
EVQLVQSGGG LVQPGGSLRL SCAGSGFTFS RNAMFWVRQA PGKGLEWVSG IGTGGATNYA    60
DSVKGRFTIS RDNAKNSLYL QMNSLRAEDM AVYYCARGRY YFDYWGQGTL VTVSS        115

SEQ ID NO: 61          moltype = AA  length = 115
FEATURE                Location/Qualifiers
REGION                 1..115
                       note = VH H1011
source                 1..115
                       mol_type = protein
                       organism = synthetic construct
SEQUENCE: 61
```

```
EVQLVQSGGG LVHPGGSLRL SCAASGFTFS RNAMFWVRQA PGKGLEWVSG IGTGGATNYA    60
DSVKGRFTIS RDNAKNSLYL QMNSLRAEDM AVYYCARGRY YFDYWGQGTL VTVSS        115

SEQ ID NO: 62              moltype = AA  length = 115
FEATURE                    Location/Qualifiers
REGION                     1..115
                           note = VH H1007
source                     1..115
                           mol_type = protein
                           organism = synthetic construct
SEQUENCE: 62
EVQLVQSGGG LVHPGGSLRL SCAGSGFTFS RNAMFWVRQA PGKGLEWVSG IGTGGATSYA    60
DSVKGRFTIS RDNAKNSLYL QMNSLRAEDM AVYYCARGRY YFDYWGQGTL VTVSS        115

SEQ ID NO: 63              moltype = AA  length = 115
FEATURE                    Location/Qualifiers
REGION                     1..115
                           note = VH H1008
source                     1..115
                           mol_type = protein
                           organism = synthetic construct
SEQUENCE: 63
EVQLVQSGGG LVHPGGSLRL SCAGSGFTFS RNAMFWVRQA PGKGLEWVSG IGTGGATNYA    60
DSVKGRFTIS RDNAKNSLYL QMNSLRAEDT AVYYCARGRY YFDYWGQGTL VTVSS        115

SEQ ID NO: 64              moltype = AA  length = 115
FEATURE                    Location/Qualifiers
REGION                     1..115
                           note = VH H1015
source                     1..115
                           mol_type = protein
                           organism = synthetic construct
SEQUENCE: 64
EVQLVESGGG LVQPGGSLRL SCAGSGFTFS RNAMFWVRQA PGKGLEWVSG IGTGGATNYA    60
DSVKGRFTIS RDNAKNSLYL QMNSLRAEDM AVYYCARGRY YFDYWGQGTL VTVSS        115

SEQ ID NO: 65              moltype = AA  length = 115
FEATURE                    Location/Qualifiers
REGION                     1..115
                           note = VH H1013
source                     1..115
                           mol_type = protein
                           organism = synthetic construct
SEQUENCE: 65
EVQLVESGGG LVHPGGSLRL SCAASGFTFS RNAMFWVRQA PGKGLEWVSG IGTGGATNYA    60
DSVKGRFTIS RDNAKNSLYL QMNSLRAEDM AVYYCARGRY YFDYWGQGTL VTVSS        115

SEQ ID NO: 66              moltype = AA  length = 115
FEATURE                    Location/Qualifiers
REGION                     1..115
                           note = VH H1014
source                     1..115
                           mol_type = protein
                           organism = synthetic construct
SEQUENCE: 66
EVQLVQSGGG LVQPGGSLRL SCAASGFTFS RNAMFWVRQA PGKGLEWVSG IGTGGATNYA    60
DSVKGRFTIS RDNAKNSLYL QMNSLRAEDM AVYYCARGRY YFDYWGQGTL VTVSS        115

SEQ ID NO: 67              moltype = AA  length = 115
FEATURE                    Location/Qualifiers
REGION                     1..115
                           note = VH H1012
source                     1..115
                           mol_type = protein
                           organism = synthetic construct
SEQUENCE: 67
EVQLVQSGGG LVHPGGSLRL SCAGSGFTFS RNAMFWVRQA PGKGLEWVSG IGTGGATSYA    60
DSVKGRFTIS RDNAKNSLYL QMNSLRAEDT AVYYCARGRY YFDYWGQGTL VTVSS        115

SEQ ID NO: 68              moltype = AA  length = 115
FEATURE                    Location/Qualifiers
REGION                     1..115
                           note = VH H1016
source                     1..115
                           mol_type = protein
                           organism = synthetic construct
SEQUENCE: 68
EVQLVQSGGG LVHPGGSLRL SCAGSGFTFS RNAMFWVRQA PGKGLEWVSG IGTGGATNYA    60
DSVKGRFTIS RDNAKNSLYL QMNSLRAEDM AVYYCARGRY YFPWWGQGTL VTVSS        115
```

-continued

```
SEQ ID NO: 69               moltype = AA  length = 115
FEATURE                     Location/Qualifiers
REGION                      1..115
                            note = VH H1017
source                      1..115
                            mol_type = protein
                            organism = synthetic construct
SEQUENCE: 69
EVQLVESGGG LVHPGGSLRL SCAGSGFTFS RNAMFWVRQA PGKGLEWVSG IGTGGATNYA 60
DSVKGRFTIS RDNAKNSLYL QMNSLRAEDM AVYYCARGRY YFPWWGQGTL VTVSS       115

SEQ ID NO: 70               moltype = AA  length = 115
FEATURE                     Location/Qualifiers
REGION                      1..115
                            note = VH H1018
source                      1..115
                            mol_type = protein
                            organism = synthetic construct
SEQUENCE: 70
EVQLVQSGGG LVQPGGSLRL SCAGSGFTFS RNAMFWVRQA PGKGLEWVSG IGTGGATNYA 60
DSVKGRFTIS RDNAKNSLYL QMNSLRAEDM AVYYCARGRY YFPWWGQGTL VTVSS       115

SEQ ID NO: 71               moltype = AA  length = 115
FEATURE                     Location/Qualifiers
REGION                      1..115
                            note = VH H1019
source                      1..115
                            mol_type = protein
                            organism = synthetic construct
SEQUENCE: 71
EVQLVQSGGG LVHPGGSLRL SCAASGFTFS RNAMFWVRQA PGKGLEWVSG IGTGGATNYA 60
DSVKGRFTIS RDNAKNSLYL QMNSLRAEDM AVYYCARGRY YFPWWGQGTL VTVSS       115

SEQ ID NO: 72               moltype = AA  length = 115
FEATURE                     Location/Qualifiers
REGION                      1..115
                            note = VH H1020
source                      1..115
                            mol_type = protein
                            organism = synthetic construct
SEQUENCE: 72
EVQLVQSGGG LVHPGGSLRL SCAGSGFTFS RNAMFWVRQA PGKGLEWVSG IGTGGATSYA 60
DSVKGRFTIS RDNAKNSLYL QMNSLRAEDM AVYYCARGRY YFPWWGQGTL VTVSS       115

SEQ ID NO: 73               moltype = AA  length = 115
FEATURE                     Location/Qualifiers
REGION                      1..115
                            note = VH H1021
source                      1..115
                            mol_type = protein
                            organism = synthetic construct
SEQUENCE: 73
EVQLVQSGGG LVHPGGSLRL SCAGSGFTFS RNAMFWVRQA PGKGLEWVSG IGTGGATNYA 60
DSVKGRFTIS RDNAKNSLYL QMNSLRAEDT AVYYCARGRY YFPWWGQGTL VTVSS       115

SEQ ID NO: 74               moltype = AA  length = 115
FEATURE                     Location/Qualifiers
REGION                      1..115
                            note = VH H1033
source                      1..115
                            mol_type = protein
                            organism = synthetic construct
SEQUENCE: 74
EVQLVQSGGG LVHPGRSLRL SCAGSGFTFS RNAMFWVRQA PGKGLEWVSG IGTGGATNYA 60
DSVKGRFTIS RDNAKNSLYL QMNSLRAEDM AVYYCARGRY YFDYWGQGTL VTVSS       115

SEQ ID NO: 75               moltype = AA  length = 115
FEATURE                     Location/Qualifiers
REGION                      1..115
                            note = VH H1034
source                      1..115
                            mol_type = protein
                            organism = synthetic construct
SEQUENCE: 75
EVQLVQSGGG LVHPGGSLRL TCAGSGFTFS RNAMFWVRQA PGKGLEWVSG IGTGGATNYA 60
DSVKGRFTIS RDNAKNSLYL QMNSLRAEDM AVYYCARGRY YFDYWGQGTL VTVSS       115

SEQ ID NO: 76               moltype = AA  length = 115
```

-continued

```
FEATURE              Location/Qualifiers
REGION               1..115
                     note = VH H1035
source               1..115
                     mol_type = protein
                     organism = synthetic construct
SEQUENCE: 76
EVQLVQSGGG LVHPGGSLRL SCAGSGFTFS RNAMHWVRQA PGKGLEWVSG IGTGGATNYA   60
DSVKGRFTIS RDNAKNSLYL QMNSLRAEDM AVYYCARGRY YFDYWGQGTL VTVSS        115

SEQ ID NO: 77         moltype = AA   length = 115
FEATURE              Location/Qualifiers
REGION               1..115
                     note = VH H1036
source               1..115
                     mol_type = protein
                     organism = synthetic construct
SEQUENCE: 77
EVQLVQSGGG LVHPGGSLRL SCAGSGFTFS RNAMFWVRQA PGEGLEWVSG IGTGGATNYA   60
DSVKGRFTIS RDNAKNSLYL QMNSLRAEDM AVYYCARGRY YFDYWGQGTL VTVSS        115

SEQ ID NO: 78         moltype = AA   length = 115
FEATURE              Location/Qualifiers
REGION               1..115
                     note = VH H1037
source               1..115
                     mol_type = protein
                     organism = synthetic construct
SEQUENCE: 78
EVQLVQSGGG LVHPGGSLRL SCAGSGFTFS RNAMFWVRQA PGKGLEWVSG IGTGGATNYA   60
DSVKGRFTIS RDEAKNSLYL QMNSLRAEDM AVYYCARGRY YFDYWGQGTL VTVSS        115

SEQ ID NO: 79         moltype = AA   length = 115
FEATURE              Location/Qualifiers
REGION               1..115
                     note = VH H1039
source               1..115
                     mol_type = protein
                     organism = synthetic construct
SEQUENCE: 79
EVQLVQSGGG LVHPGGSLRL SCAGSGFTFS RNAMFWVRQA PGKGLEWVSG IGTGGATNYA   60
DSVKGRFTIS RDNAKNSLYL QMNSLRAGDM AVYYCARGRY YFDYWGQGTL VTVSS        115

SEQ ID NO: 80         moltype = AA   length = 115
FEATURE              Location/Qualifiers
REGION               1..115
                     note = VH H1038
source               1..115
                     mol_type = protein
                     organism = synthetic construct
SEQUENCE: 80
EVQLVQSGGG LVHPGGSLRL SCAGSGFTFD DYAMFWVRQA PGKGLEWVSG IGTGGATNYA   60
DSVKGRFTIS RDNAKNSLYL QMNSLRAEDM AVYYCARGRY YFDYWGQGTL VTVSS        115

SEQ ID NO: 81         moltype = AA   length = 115
FEATURE              Location/Qualifiers
REGION               1..115
                     note = VH H1028
source               1..115
                     mol_type = protein
                     organism = synthetic construct
SEQUENCE: 81
EVQLVQSGGG LVQPGGSLRL SCAASGFTFS RNAMFWVRQA PGKGLEWVSG IGTGGATSYA   60
DSVKGRFTIS RDNAKNSLYL QMNSLRAEDT AVYYCARGRY YFPWWGQGTL VTVSS        115

SEQ ID NO: 82         moltype = AA   length = 115
FEATURE              Location/Qualifiers
REGION               1..115
                     note = VH H1027
source               1..115
                     mol_type = protein
                     organism = synthetic construct
SEQUENCE: 82
EVQLVESGGG LVHPGGSLRL SCAASGFTFS RNAMFWVRQA PGKGLEWVSG IGTGGATSYA   60
DSVKGRFTIS RDNAKNSLYL QMNSLRAEDT AVYYCARGRY YFPWWGQGTL VTVSS        115

SEQ ID NO: 83         moltype = AA   length = 115
FEATURE              Location/Qualifiers
REGION               1..115
```

-continued

```
                            note = VH H1026
source                      1..115
                            mol_type = protein
                            organism = synthetic construct
SEQUENCE: 83
EVQLVESGGG LVQPGGSLRL SCAGSGFTFS RNAMFWVRQA PGKGLEWVSG IGTGGATSYA  60
DSVKGRFTIS RDNAKNSLYL QMNSLRAEDT AVYYCARGRY YFPWWGQGTL VTVSS       115

SEQ ID NO: 84              moltype = AA   length = 115
FEATURE                    Location/Qualifiers
REGION                     1..115
                            note = VH H1030
source                      1..115
                            mol_type = protein
                            organism = synthetic construct
SEQUENCE: 84
EVQLVESGGG LVQPGGSLRL SCAASGFTFS RNAMFWVRQA PGKGLEWVSG IGTGGATNYA  60
DSVKGRFTIS RDNAKNSLYL QMNSLRAEDT AVYYCARGRY YFPWWGQGTL VTVSS       115

SEQ ID NO: 85              moltype = AA   length = 115
FEATURE                    Location/Qualifiers
REGION                     1..115
                            note = VH H1029
source                      1..115
                            mol_type = protein
                            organism = synthetic construct
SEQUENCE: 85
EVQLVESGGG LVQPGGSLRL SCAASGFTFS RNAMFWVRQA PGKGLEWVSG IGTGGATSYA  60
DSVKGRFTIS RDNAKNSLYL QMNSLRAEDM AVYYCARGRY YFPWWGQGTL VTVSS       115

SEQ ID NO: 86              moltype = AA   length = 115
FEATURE                    Location/Qualifiers
REGION                     1..115
                            note = VH H1025
source                      1..115
                            mol_type = protein
                            organism = synthetic construct
SEQUENCE: 86
EVQLVQSGGG LVHPGGSLRL SCAASGFTFS RNAMFWVRQA PGKGLEWVSG IGTGGATSYA  60
DSVKGRFTIS RDNAKNSLYL QMNSLRAEDT AVYYCARGRY YFPWWGQGTL VTVSS       115

SEQ ID NO: 87              moltype = AA   length = 115
FEATURE                    Location/Qualifiers
REGION                     1..115
                            note = VH H1024
source                      1..115
                            mol_type = protein
                            organism = synthetic construct
SEQUENCE: 87
EVQLVQSGGG LVQPGGSLRL SCAGSGFTFS RNAMFWVRQA PGKGLEWVSG IGTGGATSYA  60
DSVKGRFTIS RDNAKNSLYL QMNSLRAEDT AVYYCARGRY YFPWWGQGTL VTVSS       115

SEQ ID NO: 88              moltype = AA   length = 115
FEATURE                    Location/Qualifiers
REGION                     1..115
                            note = VH H1023
source                      1..115
                            mol_type = protein
                            organism = synthetic construct
SEQUENCE: 88
EVQLVESGGG LVHPGGSLRL SCAGSGFTFS RNAMFWVRQA PGKGLEWVSG IGTGGATSYA  60
DSVKGRFTIS RDNAKNSLYL QMNSLRAEDT AVYYCARGRY YFPWWGQGTL VTVSS       115

SEQ ID NO: 89              moltype = AA   length = 115
FEATURE                    Location/Qualifiers
REGION                     1..115
                            note = VH H1022
source                      1..115
                            mol_type = protein
                            organism = synthetic construct
SEQUENCE: 89
EVQLVQSGGG LVHPGGSLRL SCAGSGFTFS RNAMFWVRQA PGKGLEWVSG IGTGGATSYA  60
DSVKGRFTIS RDNAKNSLYL QMNSLRAEDT AVYYCARGRY YFPWWGQGTL VTVSS       115

SEQ ID NO: 90              moltype = AA   length = 115
FEATURE                    Location/Qualifiers
REGION                     1..115
                            note = VH H1032
source                      1..115
```

-continued

```
                         mol_type = protein
                         organism = synthetic construct
SEQUENCE: 90
EVQLVESGGG LVQPGGSLRL SCAASGFTFS RNAMFWVRQA PGKGLEWVSG IGTGGATNYA   60
DSVKGRFTIS RDNAKNSLYL QMNSLRAEDM AVYYCARGRY YFPWWGQGTL VTVSS        115

SEQ ID NO: 91           moltype = AA   length = 115
FEATURE                 Location/Qualifiers
REGION                  1..115
                        note = VH H1031
source                  1..115
                        mol_type = protein
                        organism = synthetic construct
SEQUENCE: 91
EVQLVESGGG LVQPGGSLRL SCAASGFTFS RNAMFWVRQA PGKGLEWVSG IGTGGATSYA   60
DSVKGRFTIS RDNAKNSLYL QMNSLRAEDT AVYYCARGRY YFDYWGQGTL VTVSS        115

SEQ ID NO: 92           moltype = AA   length = 115
FEATURE                 Location/Qualifiers
REGION                  1..115
                        note = VH H1000
source                  1..115
                        mol_type = protein
                        organism = synthetic construct
SEQUENCE: 92
EVQLVQSGGG LVHPGGSLRL SCAGSGFTFS RNAMFWVRQA PGKGLEWVSG IGTGGATNYA   60
DSVKGRFTIS RDNAKNSLYL QMNSLRAEDM AVYYCARGRY YFDYWGQGTL VTVSS        115

SEQ ID NO: 93           moltype = AA   length = 115
FEATURE                 Location/Qualifiers
REGION                  1..115
                        note = VH H1001
source                  1..115
                        mol_type = protein
                        organism = synthetic construct
SEQUENCE: 93
EVQLVESGGG LVQPGGSLRL SCAASGFTFS RNAMFWVRQA PGKGLEWVSG IGTGGATSYA   60
DSVKGRFTIS RDNAKNSLYL QMNSLRAEDT AVYYCARGRY YFPWWGQGTL VTVSS        115

SEQ ID NO: 94           moltype = AA   length = 209
FEATURE                 Location/Qualifiers
REGION                  1..209
                        note = sIL4Ralpha
source                  1..209
                        mol_type = protein
                        organism = Homo sapiens
SEQUENCE: 94
GNMKVLQEPT CVSDYMSIST CEWKMNGPTN CSTELRLLYQ LVFLLSEAHT CIPENNGGAG   60
CVCHLLMDDV VSADNYTLDL WAGQQLLWKG SFKPSEHVKP RAPGNLTVHT NVSDTLLLTW   120
SNPYPPDNYL YNHLTYAVNI WSENDPADFR IYNVTYLEPS LRIAASTLKS GISYRARVRA   180
WAQCYNTTWS EWSPSTKWHN SYREPFEQH                                     209
```